(12) United States Patent
Bonjouklian et al.

(10) Patent No.: US 7,863,310 B2
(45) Date of Patent: Jan. 4, 2011

(54) KINASE INHIBITORS

(75) Inventors: Rosanne Bonjouklian, Zionsville, IN (US); Robert Dean Dally, Indianapolis, IN (US); Alfonso de Dios, Madrid (ES); Mirian Filadelfa del Prado Catalina, Madrid (ES); Carmen Dominguez-Fernandez, Madrid (ES); Carlos Jaramillo Aguado, Madrid (ES); Beatriz Lopez de Uralde-Garmendia, Madrid (ES); Timothy Alan Shepherd, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1120 days.

(21) Appl. No.: 10/597,359

(22) PCT Filed: Jan. 21, 2005

(86) PCT No.: PCT/US2005/000024

§ 371 (c)(1),
(2), (4) Date: Jul. 21, 2006

(87) PCT Pub. No.: WO2005/080380

PCT Pub. Date: Sep. 1, 2005

(65) Prior Publication Data

US 2008/0227839 A1    Sep. 18, 2008

Related U.S. Application Data

(60) Provisional application No. 60/563,399, filed on Apr. 19, 2004.

(30) Foreign Application Priority Data

Feb. 3, 2004    (EP) .................................. 04380022

(51) Int. Cl.
*A61K 31/4184* (2006.01)
*C07D 403/02* (2006.01)

(52) U.S. Cl. ...................... 514/394; 514/322; 514/367; 546/199; 548/152; 548/202; 548/235; 548/255; 548/302.1; 548/315.1; 548/343.5; 548/364.7; 548/366.1; 548/373.1; 548/379.4

(58) Field of Classification Search ................. 514/322, 514/367, 394; 546/199; 548/152, 202, 235, 548/255, 302.1, 315.1, 343.5, 364.7, 366.1, 548/373.1, 379.4
See application file for complete search history.

(56) References Cited

U.S. PATENT DOCUMENTS

| | | | | |
|---|---|---|---|---|
| 6,040,327 | A | * | 3/2000 | De Nanteuil et al. ......... 514/394 |
| 7,320,995 | B2 | * | 1/2008 | Bonjouklian et al. ......... 514/367 |

FOREIGN PATENT DOCUMENTS

| | | |
|---|---|---|
| WO | WO-97/25045 A | 7/1997 |
| WO | WO-02/072576 A | 9/2002 |
| WO | WO-03/042211 A | 5/2003 |
| WO | WO-2004/014900 A1 | 2/2004 |

OTHER PUBLICATIONS

Bonjouklian et al. "Preparation of benzimi . . . " CA 140:;199326 (2004).*
Zubarovskii et al. "Synthesis of thiazole . . . " CA 67:116849 (1967).*
Gwaltney et al. "Preparation of substituted . . . " CA 132:137378 (2000).*
Prous et al. "Imidazole derivatives . . . " CA 145:410660(2006).*
Bonjouklian et al. "Preparation of benzimidazoles . . . " CA 140:199326 (2004).*
Kai, et al, Preparation of pyrazole derivatives as antiviral agents, Chemical Abstracts, XP002328394, CA125:247806, (1996).

* cited by examiner

*Primary Examiner*—Celia Chang
(74) *Attorney, Agent, or Firm*—Tina M. Tucker; Robert D. Titus

(57) ABSTRACT

The present invention provides kinase inhibitors of Formula I:

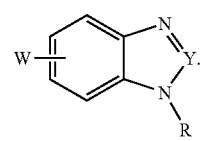

5 Claims, No Drawings

KINASE INHIBITORS

This application is a United States national phase entry, pursuant to 35 U.S.C. 371, of PCT/US2005/000024, filed Jan. 21, 2005, which claims the benefit of European Patent application No. 04380022.6, filed Feb. 03, 2004 and U.S. provisional patent application Ser. No. 60/563,399, filed Apr. 19, 2004.

BACKGROUND OF THE INVENTION

The p38 kinase is a mitogen-activated protein (MAP) kinase that belongs to the serine/threonine kinase superfamily. This kinase is activated by extracellular stresses such as heat, UV light, and osmotic stress, as well as by inflammatory stimuli such as lipopolysaccharide. When activated, p38 kinase phosphorylates intracellular protein substrates that regulate the biosynthesis of the pro-inflammatory cytokines tumor necrosis factor α (TNF-α) and interleukin-1β (IL-1β). These cytokines are implicated in the pathology of a number of chronic inflammatory disorders (Lee, et al. *Ann. N.Y. Acad. Sci.*, 696, 149-170 (1993); Muller-Ladner, *Curr. Opin. Rheumatol.* 8, 210-220 (1996)), cardiovascular and central nervous system disorders (Salituro, et al. *Current Medicinal Chemistry*, 6, 807-823 (1999)), and autoimmune disorders (Pargellis, et al., *Nature Structural Biology*, 9(4), 268-272 (2002)).

A number of compounds within the pyridinylimidazole (WO9621452, WO9725045, U.S. Pat. Nos. 5,656,644, 5,686,455, 5,717,100, WO9712876, WO9821957, WO9847892, WO99903837, WO9901449, WO0061576, WO0172737) and pyrimidinyl-imidazole (WO9725048, WO9901452, WO9725046, WO9932121, WO9901131, WO9901130, WO9901136, WO9807452, WO9747618, WO9856788, WO9857996) structural platforms have been identified as inhibitors of p38 kinase or as cytokine inhibitors. Selective inhibitors of p38 kinase are known to suppress the expression of TNF-α and IL-1β (McKenna, et al., *J. Med. Chem.* 45(11), 2173-2184 (2002)). Anti-inflammatory activity for compounds within the pyrimidinylimidazole structural platform has been reported (Lantos, et al., *J. Med. Chem.*, 27, 72-75 (1984)), and a number of inhibitors of p38 kinase are under active investigation for the treatment of a variety of disorders (Boehm and Adams, *Exp. Opin. Ther. Patents.* 10(1), 25-37 (2000)). There remains a need for treatment in this field for compounds that are cytokine suppressive drugs, i.e., compounds that are capable of inhibiting p38 kinase.

The present invention provides new inhibitors of p38 kinase useful for the treatment of conditions resulting from excessive cytokine production.

BRIEF SUMMARY OF THE INVENTION

The present invention provides compounds of Formula I:

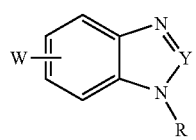

I where:
W is a ring selected from the group consisting of:

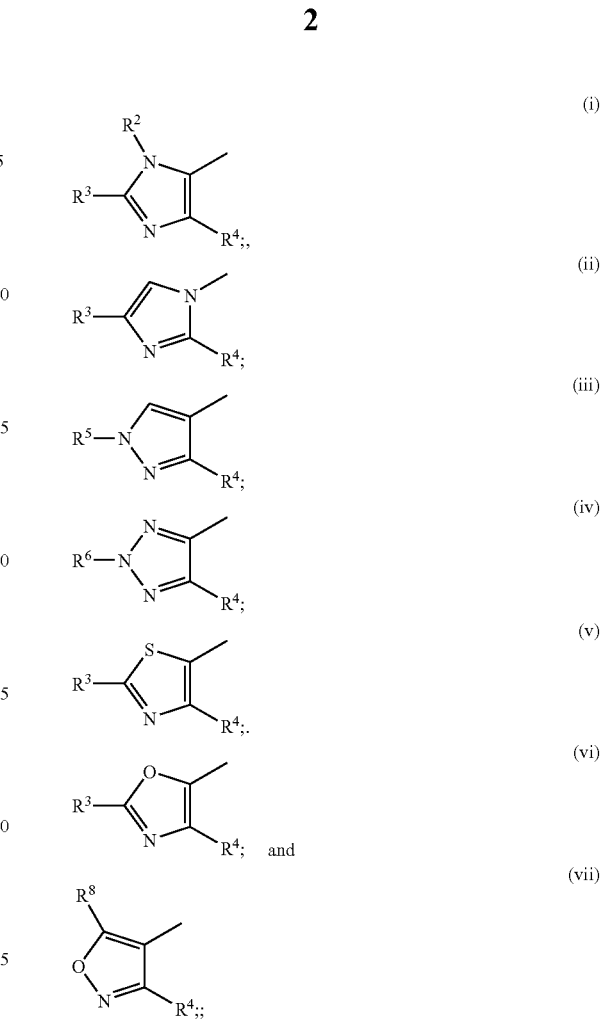

Y is N or C—$R^1$;
R is $C_1$-$C_8$ alkyl, $C_3$-$C_6$ cycloalkyl, ($C_1$-$C_4$ alkylene)-($C_3$-$C_6$ cycloalkyl), $SO_2R^7$, phenyl, or benzyl optionally substituted on the phenyl ring with one or two substituents selected from halo;
$R^1$ is hydrogen, amino, or methyl;
$R^2$ is hydrogen, $C_1$-$C_6$ alkyl, or $C_3$-$C_6$ cycloalkyl;
$R^3$ is hydrogen, $C_1$-$C_6$ alkyl, $C_3$-$C_6$ cycloalkyl, trifluoromethyl, or phenyl optionally substituted with one or two substituents independently selected from the group consisting of halo, trifluoromethyl, ($C_1$-$C_6$ alkyl)thio, 1-(pyrrolidin-1-yl)eth-2-oxy, and 1-(piperidin-1-yl)eth-2-oxy; or
$R^2$ and $R^3$ taken together form either the group —$(CH_2)_n$— where n is 2 or 3 or the group —CH=CH—;
$R^4$ is phenyl optionally substituted with one or two substituents independently selected from the group consisting of halo and trifluoromethyl;
$R^5$ is hydrogen, $C_1$-$C_6$ alkyl, $C_3$-$C_6$ cycloalkyl, or phenyl optionally substituted with one or two substituents independently selected from the group consisting of halo, trifluoromethyl, ($C_1$-$C_6$ alkyl)thio, 1-(pyrrolidin-1-yl)eth-2-oxy, and 1-(piperidin-1-yl)eth-2-oxy;
$R^6$ is hydrogen or ethoxymethyl;
$R^7$ is $C_1$-$C_4$ alkyl, $C_3$-$C_6$ cycloalkyl or dialkylamino where each alkyl group is independently selected from $C_1$-$C_4$ alkyl;
$R^8$ is hydrogen or $C_1$-$C_4$ alkyl; provided that:
(a) when W is (i), then at least one of $R^2$ and $R^3$ is hydrogen or methyl; and (b) R may be $SO_2R^7$ only when either W is isoxazole (vii) or Y is N, or R may be $SO_2R^7$ when both W is isoxazole (vii) and Y is N;

or a pharmaceutically acceptable salt thereof.

The present invention provides a method of inhibiting p-38 kinase in a mammal comprising administering to a mammal in need of such treatment an effective amount of a compound of Formula I or a pharmaceutically acceptable salt thereof.

The present invention also provides a method of suppressing the production of tumor necrosis factor α (TNF-α) in a mammal comprising administering to a mammal in need of such treatment an effective amount of a compound of Formula I or a pharmaceutically acceptable salt thereof.

The present invention also provides a method of suppressing the production of interleukin-1β (IL-1β) in a mammal comprising administering to a mammal in need of such treatment an effective amount of a compound of Formula I or a pharmaceutically acceptable salt thereof.

The present invention further provides a method of treating conditions resulting from excessive cytokine production in a mammal comprising administering to a mammal in need of such treatment a cytokine-suppressing amount of a compound of Formula I or a pharmaceutically acceptable salt thereof.

The present invention also provides a method of inhibiting the growth of a susceptible neoplasm in a mammal comprising administering to a mammal in need of such treatment a p38 inhibiting amount of a compound of Formula I or a pharmaceutically acceptable salt thereof.

The present invention also provides a method of inhibiting metastasis in a mammal comprising administering to a mammal in need of such treatment a p38 inhibiting amount of a compound of Formula I or a pharmaceutically acceptable salt thereof.

The present invention also provides a method of treating rheumatoid arthritis in a mammal comprising administering to a mammal in need of such treatment a p38 inhibiting amount of a compound of Formula I or a pharmaceutically acceptable salt thereof.

The present invention also provides a pharmaceutical formulation comprising a compound of Formula I or a pharmaceutically acceptable salt thereof, in combination with a pharmaceutically acceptable carrier, diluent or excipient.

This invention also provides the use of a compound of Formula I or a pharmaceutically acceptable salt thereof for the manufacture of a medicament for the inhibition of p38 kinase. Additionally, this invention provides a compound of Formula I or a pharmaceutically acceptable salt thereof for use in the inhibition of p38 kinase in mammals. Furthermore, this invention provides a pharmaceutical composition adapted for the inhibition of p38 kinase comprising a compound of Formula I or a pharmaceutically acceptable salt thereof in combination with one or more pharmaceutically acceptable excipients, carriers, or diluents thereof.

This invention also provides the use of a compound of Formula I or a pharmaceutically acceptable salt thereof for the manufacture of a medicament for the suppression of the production of tumor necrosis factor α (TNF-α). Additionally, this invention provides a compound of Formula I or a pharmaceutically acceptable salt thereof for use in the suppression of the production of tumor necrosis factor α (TNF-α) in mammals. Furthermore, this invention provides a pharmaceutical composition adapted for the suppression of the production of tumor necrosis factor α (TNF-α) comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the suppression of the production of interleukin-1β (IL-1β). Additionally, this invention provides a compound of Formula I or a pharmaceutically acceptable salt thereof for use in the suppression of the production of interleukin-1β (IL-1β) in mammals. Furthermore, this invention provides a pharmaceutical composition adapted for the suppression of the production of interleukin-1β (IL-1β) comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the treatment of conditions resulting from excessive cytokine production. Additionally, this invention provides a compound of Formula I or a pharmaceutically acceptable salt thereof for use in the treatment of conditions resulting from excessive cytokine production in mammals. Furthermore, this invention provides a pharmaceutical composition adapted for the treatment of conditions resulting from excessive cytokine production comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of growth of a susceptible neoplasm. Additionally, this invention provides a compound of Formula I or a pharmaceutically acceptable salt thereof for use in the inhibition of growth of a susceptible neoplasm in, mammals. Furthermore, this invention provides a pharmaceutical composition adapted for the inhibition of growth of a susceptible neoplasm comprising a compound of Formula I or a pharmaceutically acceptable salt thereof in combination with one or more pharmaceutically acceptable excipients, carriers, or diluents.

This invention also provides the use of a compound of Formula I or a pharmaceutically acceptable salt thereof for the manufacture of a medicament for the inhibition of metastasis. Additionally, this invention provides a compound of Formula I or a pharmaceutically acceptable salt thereof for use in the inhibition of metastasis in mammals. Furthermore, this invention provides a pharmaceutical composition adapted for the inhibition of metastasis comprising a compound of Formula I or a pharmaceutically acceptable salt thereof in combination with one or more pharmaceutically acceptable excipients, carriers, or diluents. The invention also provides the use of a compound of Formula I for the manufacture of a medicament for treating a disease or condition capable of being improved or prevented by inhibition of p-38 kinase.

This invention also provides the use of a compound of Formula I or a pharmaceutically acceptable salt thereof for the manufacture of a medicament for the treatment of rheumatoid arthritis. Additionally, this invention provides a compound of Formula I or a pharmaceutically acceptable salt thereof for use in the treatment of rheumatoid arthritis in mammals. Furthermore, this invention provides a pharmaceutical composition adapted for the treatment of rheumatoid arthritis comprising a compound of Formula I or a pharmaceutically acceptable salt thereof in combination with one or more pharmaceutically acceptable excipients, carriers, or diluents.

DETAILED DESCRIPTION OF THE INVENTION

The general chemical terms used in the formulae above have their usual meanings. For example, the term "$C_1$-$C_8$ alkyl" includes methyl, ethyl, propyl, isopropyl, butyl, isobutyl, sec-butyl, tert-butyl, pentyl, neopentyl, hexyl, and octyl moieties. The term "$C_3$-$C_6$ cycloalkyl" includes cyclopropyl, cyclobutyl, cyclopentyl, and cyclohexyl moieties. The term "halo" includes fluoro, chloro, bromo, and iodo.

The term "p-38 kinase" is taken to mean the p-38α and/or p-38β kinase isoforms.

The term "suppressing the production of TNF-α (IL-1β, cytokine)" is taken to mean decreasing of excessive in vivo levels of TNF-α, IL-1β, or another cytokine in a mammal to normal or sub-normal levels. This may be accomplished by inhibition of the in vivo release of TNF-α, IL-1β, or another cytokine by all cells, including macrophages; by down regulation, at the genomic level, of excessive in vivo levels of TNF-α, IL-1β, or another cytokine in a mammal to normal or sub-normal levels; by inhibition of the synthesis of TNF-α, IL-1β, or another cytokine as a posttranslational event; or by a down regulation of TNF-α, IL-1β, or another cytokine at the translational level.

The skilled artisan will appreciate that certain compounds of Formula I contain at least one chiral center. The present invention contemplates all individual enantiomers or diastereomers, as well as mixtures of the enantiomers and diastereomers of said compounds including racemates. It is preferred that compounds of Formula I containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques.

The substituent W is bonded to the phenyl ring of the benzofused moiety of compounds of Formula I in a manner giving rise to two regioisomeric forms represented by the following structural formulae:

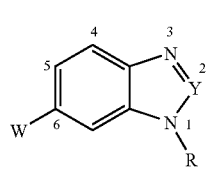

Regioisomer I

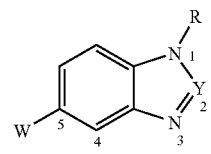

Regioisomer II

These isomeric forms give rise to two different numbering conventions. When the compounds of Formula I exist in the form of Regioisomer I, the substituent "W" will be attached at the 6-position of the ring. When the compounds of Formula I exist in the form of Regioisomer II, the substituent "W" will be attached at the 5-position of the ring. Likewise, the skilled artisan will appreciate that when W is imidazole (i), and $R^2$ is hydrogen, the imidazole ring exists in two tautomeric forms. Also when W is pyrazole (iii) or triazole (iv), the pyrazole exists in two tautomeric forms and the triazole exists in three tautomeric forms. All of these tautomeric forms and the resulting regioisomers are contemplated by the present invention, and are included in the meaning of the compounds represented by Formula I. Compounds of Formula I represented by Regioisomer I represent a preferred embodiment of the present invention.

It will be understood by the skilled reader that most or all of the compounds of the present invention are capable of forming salts. In all cases, the pharmaceutically acceptable salts of all of the compounds are included in the names of them. The compounds of the present invention are amines, and accordingly react with any of a number of inorganic and organic acids to form pharmaceutically acceptable acid addition salts. Preferred pharmaceutically acceptable salts are those formed with hydrochloric acid and methanesulfonic acid.

While all of the compounds of Formula I are useful inhibitors of p-38 kinase, certain classes of compounds are preferred. The following paragraphs describe such preferred classes:

a) W is imidazole (i);
b) W is pyrazole (iii);
c) R is $C_1$-$C_8$ alkyl;
d) R is isobutyl;
e) R is 2,2-dimethylpropyl;
f) $R^1$ is amino;
g) $R^2$ is hydrogen;
h) $R^3$ is phenyl substituted with one or two substituents independently selected from halo;
i) $R^3$ is phenyl substituted with two substituents independently selected from halo;
j) $R^3$ is phenyl disubstituted with fluoro;
k) $R^3$ is 2,6-difluorophenyl;
l) $R^3$ is 2-fluoro-6-chlorophenyl;
m) $R^4$ is phenyl;
n) the compound of Formula I is a free base;
o) the compound of Formula I is a pharmaceutically acceptable salt;
p) the compound of Formula I is the hydrochloride salt;
q) the compound of Formula I is the methanesulfonate salt;
r) Y is C—$R^1$.

Preferred embodiments of the present invention include all combinations of paragraphs a)-r). Preferred compounds of Formula I are those where R is $C_1$-$C_8$ alkyl, $C_3$-$C_6$ cycloalkyl, ($C_1$-$C_4$ alkylene)-($C_3$-$C_6$ cycloalkyl), phenyl, or benzyl optionally substituted on the phenyl ring with one or two substituents selected from halo. More preferred compounds of Formula I are those where R is $C_1$-$C_8$ alkyl. Especially preferred compounds of Formula I are those in the form of Regioisomer I, W is imidazole (i), R is $C_1$-$C_8$ alkyl, $R^2$ is hydrogen, $R^3$ is phenyl substituted with one or two substituents selected from halo, Y is C—$R^1$, and $R^1$ is amino.

The compounds of Formula I are inhibitors of p38 kinase. Thus, the present invention also provides a method of inhibiting p38 kinase in a mammal that comprises administering to a mammal in need of said treatment a p38 kinase-inhibiting amount of a compound of Formula I. It is preferred that the mammal to be treated by the administration of the compounds of Formula I is human.

As inhibitors of p38 kinase, the compounds of the present invention are useful for suppressing the production of the pro-inflammatory cytokines tumor necrosis factor α (TNF-α) and interleukin-1β (IL-1β), and therefore for the treatment of disorders resulting from excessive cytokine production. The present compounds are therefore believed to be useful in treating inflammatory disorders, including eczema, atopic dermatitis, rheumatoid arthritis, osteoarthritis, inflammatory bowel disease, and toxic shock syndrome. The compounds of the present invention are also believed to be useful in the treatment of cardiovascular disorders, such as acute myocardial infarction, chronic heart failure, atherosclerosis, viral myocarditis, cardiac allograft rejection, and sepsis-associated cardiac dysfunction. Furthermore, the compounds of the present invention are also believed to be useful for the treatment of central nervous system disorders, such as meningococcal meningitis, Alzheimer's disease, Parkinson's disease, and multiple sclerosis.

Most solid tumors increase in mass through the proliferation of malignant cells and stromal cells, including endothelial cells. In order for a tumor to grow larger than 2-3 millimeters in diameter, it must form a vasculature, a process known as angiogenesis. Suppression of tumor-induced angiogenesis by angiostatin and endostatin has been reported to result in antitumor activity (O'Reilly, et al, *Cell* 88, 277-285 (1997)). The selective p38 kinase inhibitor SB22025 has been shown to inhibit angiogenesis (J. R. Jackson, et al., *J. Pharmacol. Exp. Therapeutics* 284, 687 (1998)). Because angiogenesis is a critical component of the mass expansion of most solid tumors, the development of new p38 kinase inhibitors for the inhibition of this process represents a promising approach for antitumor therapy. This approach to antitumor therapy may lack the toxic side effects or drug resistance-inducing properties of conventional chemotherapy (Judah Folkman, *Endogenous Inhibitors of Angiogenesis*, The Harvey Lectures, Series 92, pages 65-82, Wiley-Liss Inc., (1998)).

As inhibitors of p38 kinase, the compounds of the present invention, therefore, are also useful in inhibiting growth of susceptible neoplasms. Schultz, R. M. *Potential of p38 MAP kinase inhibitors in the treatment of cancer*. In: E. Jucker (ed.), *Progress in Drug Research*, 60, 59-92, (2003). A susceptible neoplasm is defined to be a neoplasm that depends upon p38 kinase for its survival, growth, or metastasis. Susceptible neoplasms include tumors of the brain, genitourinary tract, lymphatic system, stomach, larynx, and lung (U.S. Pat. No. 5,717,100). Preferably, the term "susceptible neoplasms" as used in the present application includes human cancers including non-small cell lung carcinoma (A. Greenberg, et al., *Am. J. Respir. Cell Mol. Biol.* 26, 558 (2002)), breast carcinoma (J. Chen, et al., *J. Biol. Chem.*, 276, 47901 (2001); B. Salh, et al., *Int. J. Cancer*, 98, 148 (2002); and S. Xiong, et al., *Cancer Res.*, 61, 1727 (2001)), gastric carcinoma (Y. D. Jung, et al., *Proc. Am. Assoc. Cancer Res.* 43, 9 (2002)), colorectal carcinomas (S. Xiong, et al., *Cancer Res.*, 61, 1727 (2001)), prostate carcinomas (J-I Park, et al, *Oncogene*, 22, 4314-4332 (2003); L. Chen, et al, *Cancer Lett.*, 215, 239-247 (2004); and A. R. Uzgara, et al., *Prostate* 55, 128-139 (2003)), multiple myeloma (Hideshima, et al., *Oncogene* advance online publication, 1-11, (11 Oct. 2004); and Hideshima, et al., *Blood*, 101(2), 703 (2003)), and malignant melanoma (C. Denkert, et al., *Clin. Exp. Metastasis*, 19, 79 (2002)).

Inhibition of angiogenesis by suppression of TNF-α has also been taught to be useful in the inhibition or prevention of metastasis (U.S. Pat. No. 6,414,150; U.S. Pat. No. 6,335,336). Furthermore, suppression of TNF-α is indicated for the treatment and prevention of cachexia, a wasting syndrome experienced by about half of all cancer patients (T. Yoneda, et al., *J. Clin. Invest.*, 87, 977 (1991)).

Furthermore, inhibition of p38 kinase may be effective in the treatment of certain viral conditions such as influenza (K. Kujime, et al., *J. Immunology.*, 164, 3222-3228 (2000)), rhinovirus (S. Griego, et al. *J. Immunology*, 165, 5211-5220 (2000)), and HIV (L. Shapiro, et al., *Proc. Natl. Acad. Sci. USA*, 95, 7422-7426, (1998)).

The compounds of the present invention can be prepared by a variety of procedures, some of which are illustrated in the Schemes below. It will be recognized by one of skill in the art that the individual steps in the following schemes may be varied to provide the compounds of Formula I. The particular order of steps required to produce the compounds of Formula I is dependent upon the particular compound being synthesized, the starting compound, and the relative lability of the substituted moieties. Some substituents have been eliminated in the following schemes for the sake of clarity and are not intended to limit the teaching of the schemes in any way.

Compounds of Formula I where W is the imidazole (i) and Y is N or C—NH$_2$ may be prepared as illustrated in the following scheme where "TBS" is defined to be tert-butyldimethylsilyl and variables Y, R, R$^3$, and R$^4$ are as previously defined.

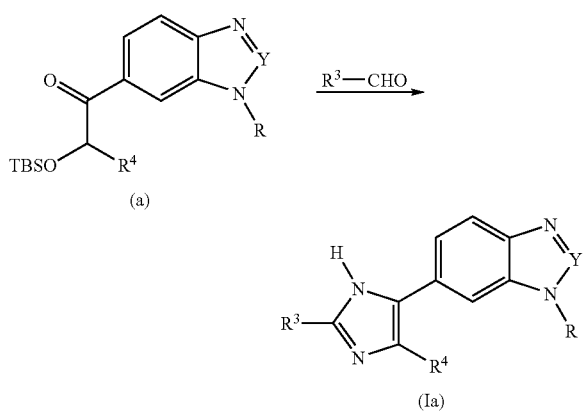

Scheme I

A mixture of the α-ketosilylether (a) is heated with an appropriate aldehyde in the presence of copper(II) acetate and ammonium acetate in a suitable solvent, typically acetic acid. The acid is neutralized and the desired imidazole (Ia) isolated by standard extractive and chromatographic techniques.

The requisite α-ketosilylether (a) may be prepared as described in the following scheme where "TBS" and variables R, R$^3$, and R$^4$ are as previously defined, and Y is N or C—NH$_2$.

Scheme II

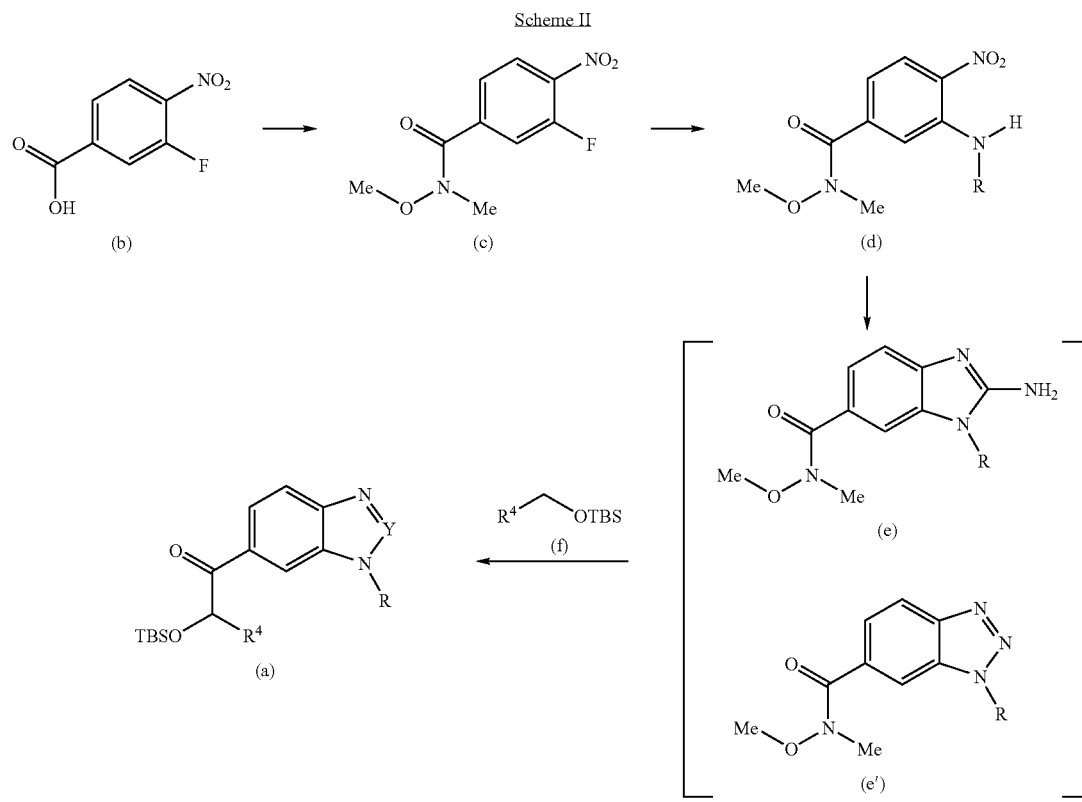

3-Fluoro-4-nitrobenzoic acid (b) is converted to the corresponding Weinreb amide (c) under standard conditions. Briefly, benzoic acid (b) is reacted with N,O-dimethyl-hydroxylamine hydrochloride in the presence of 1-(3-dimethylaminopropyl)-3-ethylcarbodiimide hydrochloride and 4-dimethylaminopyridine in a suitable solvent, preferably dichloromethane. The desired Weinreb amide (c) is isolated by standard extractive and chromatographic techniques. The Weinreb amide (c) is reacted with an appropriate amine in an appropriate solvent to provide the substituted nitroaniline (d). The substituted nitroaniline (d) is first hydrogenated to form the corresponding diamine, and is then reacted with either cyanogen bromide in the presence of a suitable base to provide the corresponding aminobenzimidazole (e), or is reacted with an appropriate nitrite to provide the corresponding benzotriazole (e'). The aminobenzimidazole (e) or benzotriazole (e') is reacted with the anion generated from the silyl ether (f) and tert-butyllithium to provide the desired intermediate (a). The requisite silyl ether (f) may be prepared from the corresponding alcohol under standard conditions (see, Greene, et al, *Protective Groups in Organic Synthesis*, John Wiley and Sons Ed., 1981).

Alternatively, compounds of Formula I where W is the imidazole (i) may be prepared as illustrated in the following scheme where R, $R^1$, $R^3$, and $R^4$ are as previously defined.

Scheme III

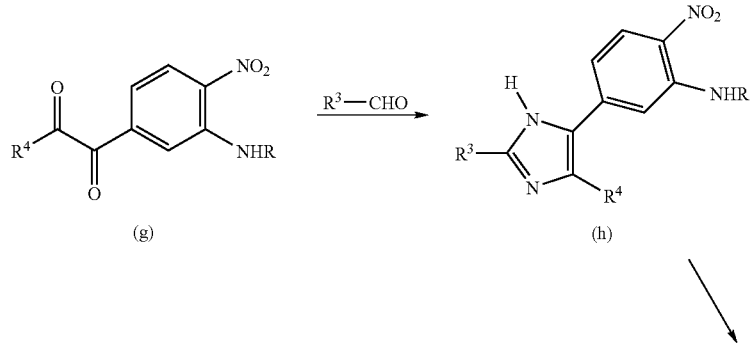

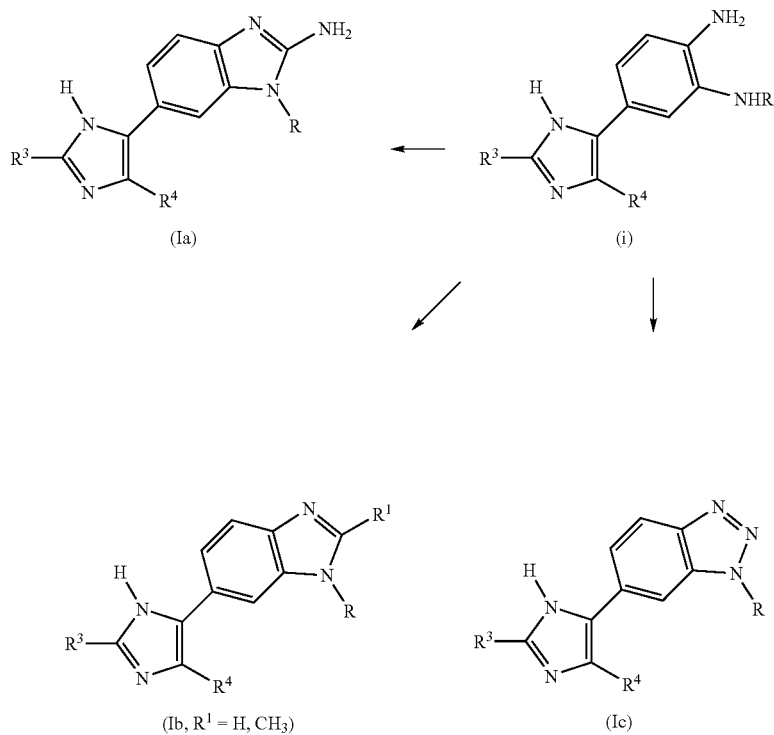

(Ia)

(i)

(Ib, R¹ = H, CH₃)

(Ic)

Diketone (g) is reacted with ammonium acetate and an appropriate aldehyde in an appropriate solvent, preferably acetic acid, to provide the corresponding nitrophenylimidazole (h). The nitro moiety is reduced under standard hydrogenation or chemical conditions to provide the corresponding diamine (j) This diamine is then either reacted with cyanogen bromide to provide the 6-(imidazol-5-yl)-2-aminobenzimidazole (Ia), with an appropriate orthoformate to provide the 6-(imidazol-5-yl)benzimidazole (Ib), or with an appropriate nitrite to provide the 6-(imidazol-5-yl)benzotriazole (Ic). The skilled artisan will appreciate that the corresponding 5-(imidazol-5-yl)-benzimidazoles and benzotriazoles may be prepared by beginning with the 3-nitro-4-NHR-diketone isomer of intermediate (g).

The requisite diketones (g) may be prepared as described in the following scheme, where $R^4$ is as previously defined.

Scheme IV

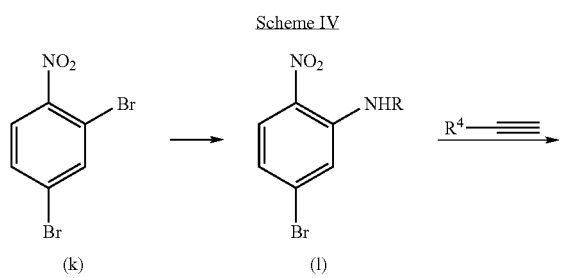

(k)

(l)

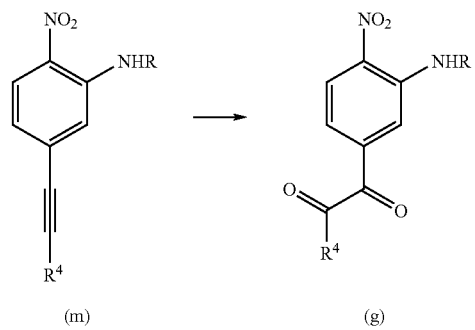

(m)

(g)

2,4-Dibromonitrobenzene (k) and an appropriate amine or amine derivative are heated together in an appropriate solvent to provide the corresponding 2-amino-4-bromonitrobenzene (l), which is then coupled with an appropriately substituted acetylene to provide the corresponding 1,2-disubstituted acetylene (m). This acetylene is oxidized to provide the target diketone (g).

Compounds of Formula I where W is imidazole (i) and $R^2$ is cycloalkyl may be prepared as described in the following scheme where variables $R^3$, and $R^4$ are as previously defined.

Scheme V

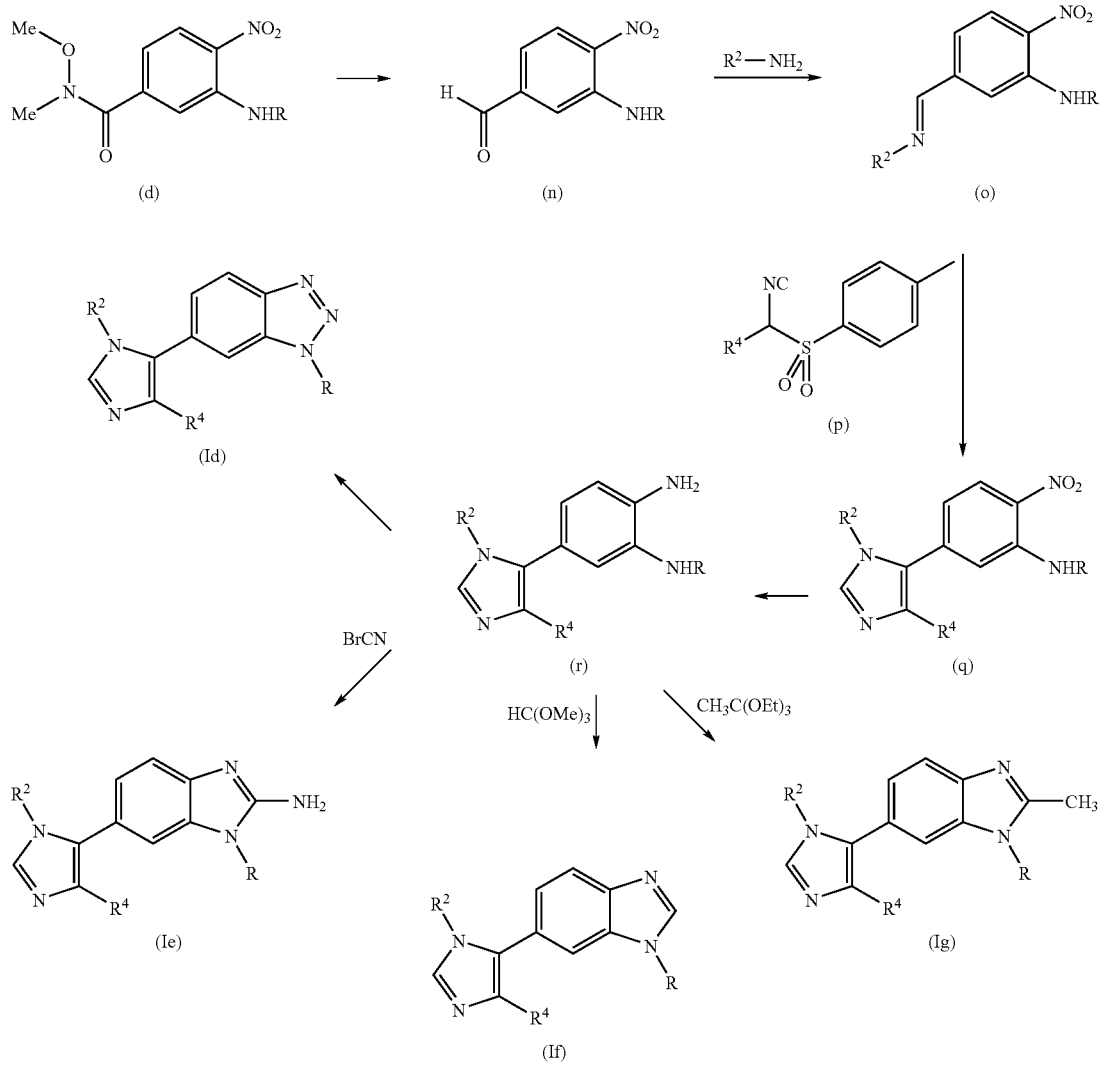

Weinreb amide (d) is treated with an appropriate hydride reducing agent, preferably lithium aluminum hydride, at low temperature in a suitable solvent, preferably tetrahydrofuran, to provide the aldehyde (n). Aldehyde (n) is reacted with an appropriate amine or amine derivative in a suitable solvent, typically dimethylformamide, to provide the corresponding aldimine (o). This imine is then reacted with an appropriately substituted p-toluene-sulfonylmethyl isocyanate (p) in a suitable solvent, typically methanol, at reflux to form the imidazole ring (q). The nitro group is reduced as previously described to provide the diamine (r). This diamine is then reacted with an appropriate nitrite, cyanogen bromide, trimethylortho-formate, or triethylorthoformate as previously described to provide compounds Id, Ie, If, and Ig, respectively. The requisite amines are either commercially available or may be prepared by methods well known to the skilled artisan. The requisite amine derivatives, such as sulfonamides, are either commercially available or may be prepared by methods well known to the skilled artisan. The requisite p-toluenesulfonylmethyl isocyanates (p) may be prepared as described in the following scheme where the variable $R^4$ is as previously defined.

Scheme VI

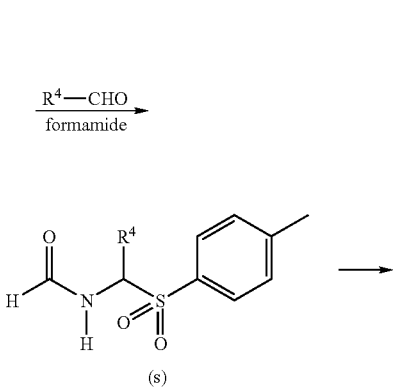

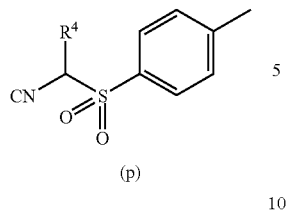

(p)

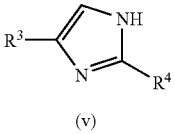

(v)

A mixture of p-toluenesulfinic acid, formamide, and an appropriate aldehyde are combined and heated together in the presence of a suitable acid to provide the N-formyl p-toluenesulfonylmethylamine (s). The intermediate (s) is reacted with a suitable dehydrating agent, typically phosphorus oxychloride, to provide the isocyanide (p). The requisite aldehydes are either commercially available or may be prepared by standard methods well known in the art.

Analogously, compounds of Formula I where W is imidazole (i) and $R^2$ is alkyl may be prepared beginning with an appropriately substituted formylbenzimidazole or formylbenzotriazole. The corresponding imine is prepared by reaction with an appropriate amine, and is then reacted with an appropriate p-toluenesulfonylmethyl isocyanate as described in Scheme V. Various $R^3$ substituents may be introduced using standard methodology, for example, by bromination followed by palladium coupling.

Additional compounds of Formula I where W is imidazole (i) or isoxazole (vii) may be prepared under standard palladium coupling conditions as described in the following Scheme, where W' is imidazole (i) or isoxazole (vii), and Y and R are as previously defined.

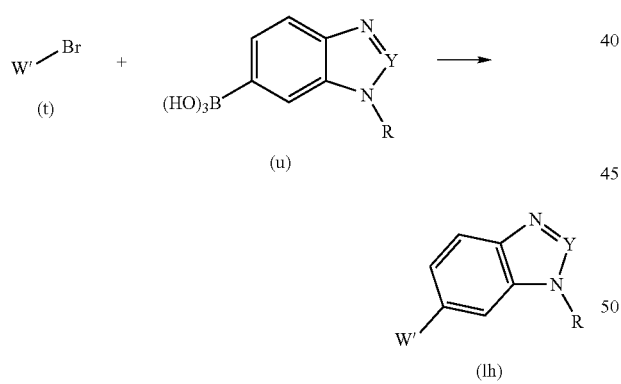

An appropriately substituted haloheteroaryl (t) is coupled with an appropriately substituted (benzimidazolyl)boronic acid (u) in the presence of a palladium catalyst, typically bis(triphenylphosphine)palladium(II) chloride, in a suitable solvent to provide the desired compound of Formula Ih. The requisite starting materials are either commercially available or may be prepared by methods well known to one of ordinary skill in the art.

Compounds of Formula I where W is imidazole (ii) may be prepared as illustrated in the following Scheme, where variables Y, R, $R^3$, and $R^4$ are as previously defined.

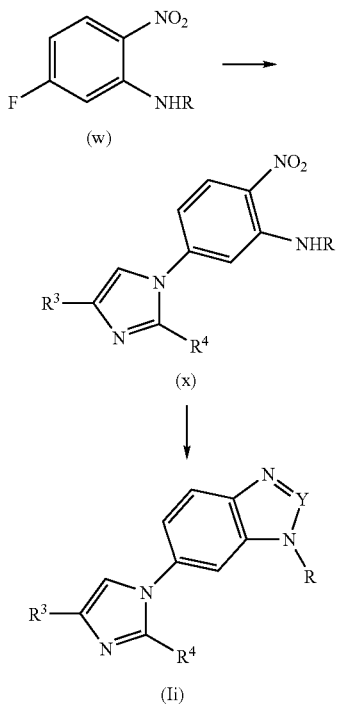

Imidazole (v) is reacted with fluorobenzene (w) in the presence of a suitable base, typically potassium carbonate, to provide the substituted imidazole (x). The desired benzimidazoles and benzotriazoles (Ii) are prepared as previously described.

Compounds of Formula I where W is pyrazole (iii) are prepared as described in the following Scheme where Y, R, and $R^4$ are as previously defined.

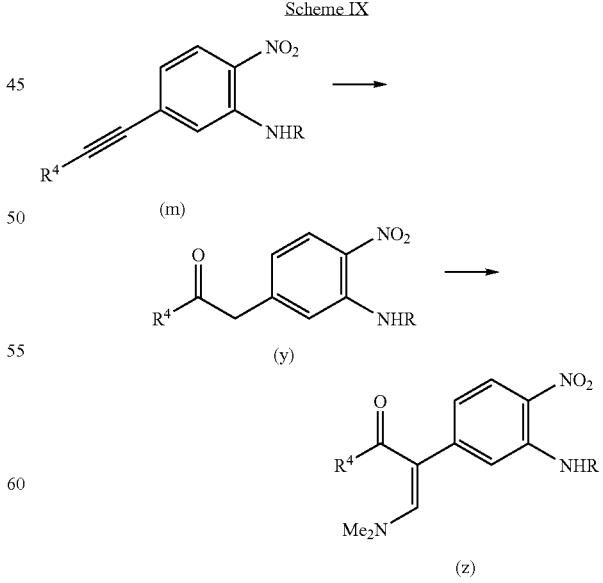

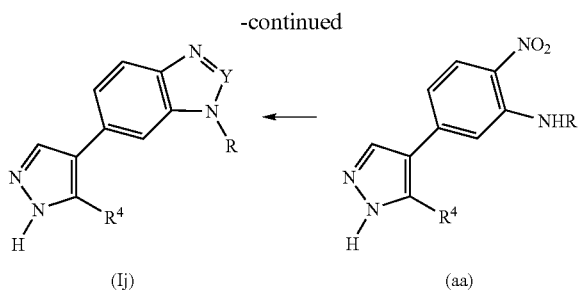

Acetylene (m) is treated with mercuric oxide in aqueous sulfuric acid to provide the benzyl ketone (y). This ketone is treated with dimethylformamide dimethylacetal or tris(dimethylamino)methane in a suitable solvent, typically dimethylformamide, to provide the enaminoketone (z). The enaminoketone is then treated with hydrazine in a suitable solvent, typically ethanol or methanol, to provide the phenylpyrazole (aa). The benzimidazole moiety is prepared as previously described to provide the compounds of Formula Ij.

The compounds of Formula I where W is the [1,2,3]triazole (iv) may be prepared as described in the following Scheme where variables Y, R, and $R^4$ are as previously defined.

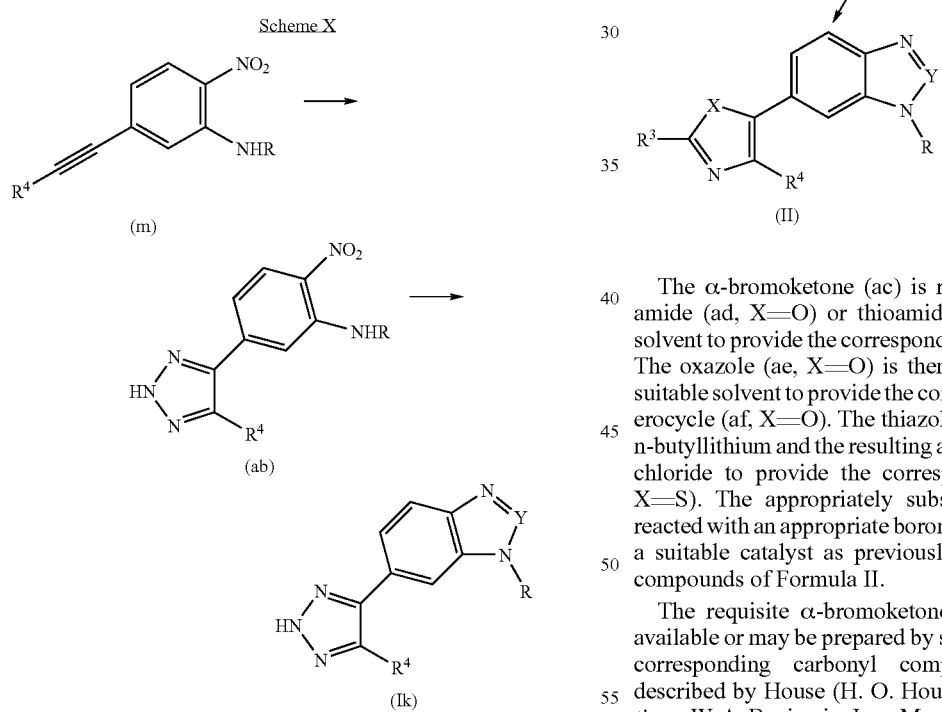

The acetylene (m) is reacted with a source of azide, typically sodium azide, in a suitable solvent, such as dimethyoxyethane to provide the phenyltriazole (ab). The benzimidazole or benzotriazole moiety is prepared as previously described to provide the compounds of Formula Ik.

The compounds of Formula I where W is the thiazole (v) or oxazole (vi) may be prepared as described in the following Scheme where variables Y, R, $R^3$, and $R^4$ are as previously defined and X is O or S.

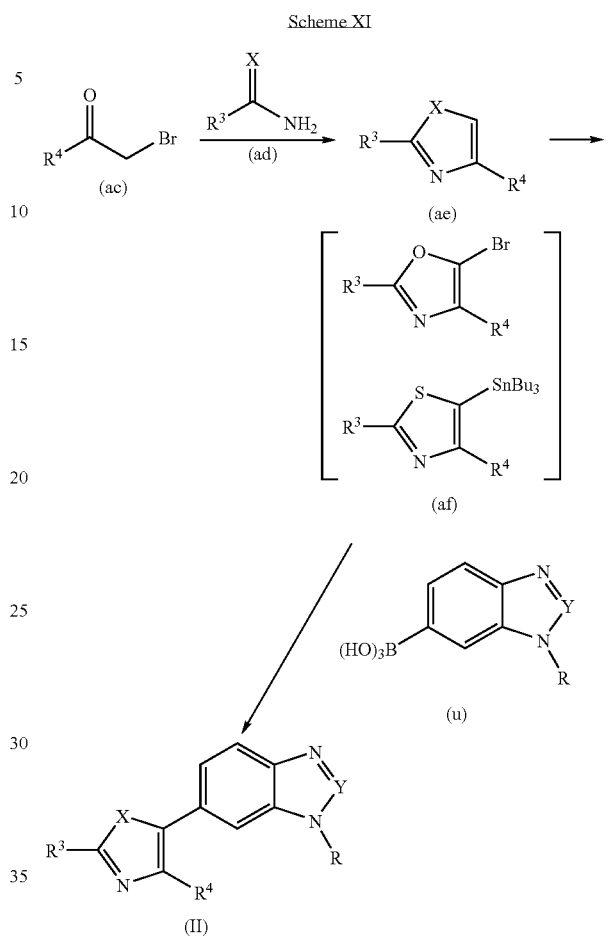

The α-bromoketone (ac) is reacted with an appropriate amide (ad, X=O) or thioamide (ad, X=S) in a suitable solvent to provide the corresponding oxazole or thiazole (ae). The oxazole (ae, X=O) is then treated with bromine in a suitable solvent to provide the corresponding brominated heterocycle (af, X=O). The thiazole (ac, X=S) is treated with n-butyllithium and the resulting anion reacted with tributyltin chloride to provide the corresponding tin derivative (aft X=S). The appropriately substituted heterocycle (af) is reacted with an appropriate boronic acid (u) in the presence of a suitable catalyst as previously described to provide the compounds of Formula II.

The requisite α-bromoketones are either commercially available or may be prepared by standard conditions from the corresponding carbonyl compound, for example, as described by House (H. O. House, *Modern Synthetic Reactions*, W. A. Benjamin, Inc., Menlo Park, Calif. (1972), pages 459-478) and Larock (R. C. Larock, *Comprehensive Organic Transformations*, VCH Publishers, Inc., New York, N.Y. (1989), pages 369-471, 755). The requisite amides and thioamides are either commercially available or may be prepared by standard methods well known to the skilled artisan.

Many of the compounds of the present invention are not only inhibitors of p38 kinase, but are also useful intermediates for the preparation of additional compounds of the present invention. For example, primary and secondary amines may be acylated, alkylated or coupled with carboxylic acids or amino acids under standard peptide coupling conditions. Furthermore, ester moieties may be reduced to the corresponding alcohols or converted to amides under standard conditions. Alcohols may be activated and displaced by a number of nucleophiles to provide other compounds of the invention. Such leaving groups include but are not limited to halides, oxonium ions, alkyl perchlorates, ammonioalkanesulfonate esters, alkyl fluorosulfonates, nonaflates, tresylates, triflates, and sulfonic esters, preferably the mesylate or tosylate. Techniques for the introduction of these groups are also well known to the skilled artisan; see, for example, March, *Advanced Organic Chemistry,* 5th Ed., John Wiley and Sons, New York, pg. 445-449 (2001). Additionally, the 2-amino moiety of the benzimidazole nucleus may be diazotized and displaced to provide additional compounds of the invention under standard conditions.

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired. The skilled artisan will appreciate that the protecting groups may be removed at any convenient point in the synthesis of the compounds of the present invention. Methods for introducing and removing nitrogen and oxygen protecting groups are well known in the art; see, for example, Greene and Wuts, *Protective Groups in Organic Synthesis* 3rd Ed., John Wiley and Sons, New York, Chapter 7 (1999). Furthermore, the skilled artisan will appreciate that in many circumstances, the order in which moieties are introduced is not critical. The particular order of steps required to produce the compounds of Formula I is dependent upon the particular compound being synthesized, the starting compound, and the relative lability of the substituted moieties.

The abbreviations, symbols and terms used in the preparations and examples have the following meanings: n-BuLi=n-butyllithium, t-BuOK=potassium tert-butoxide, DME=ethylene glycol dimethyl ether, DMF=N,N-diethylformamide, DMSO=dimethylsulfoxide, EtOAc=ethyl acetate, h=hour(s), hex=hexanes, $PdCl_2(PPh_3)_2$=dichlorobis(triphenylphosphine)palladium (II), $Pd(OAc)_2$=palladium acetate, $P(t-Bu)_3$=tri-t-butylphosphine, quant=quantitative, RT=room temperature, and THF=tetrahydrofuran.

Preparation 1

1-(2-Amino-1-cyclopentyl-1H-benzimidazol-6-yl)-2-(tert-butyldimethylsilyl)oxy-2-(phenyl)ethan-1-one N-[methyl]N-[methoxy]3-fluoro-4-nitrobenzamide Dissolve 3-Fluoro-4-nitro-benzoic acid (10.7 g, 57.71 mmol) in 1000 mL anhydrous dichloromethane. Add N,O-Dimethylhydroxylamine hydrochloride (4.5 g, 46.17 mmol), followed by 1-(3 dimethylaminopropyl)-3-ethylcarbodiimide hydrochloride (16.60 g, 86.57 mmol) and 4 diethylaminopyridine (6.77 g, 55.4 mmol). Stir at room temperature under nitrogen atmosphere overnight. Concentrate under reduced pressure and partition the residue between ethyl acetate (300 mL) and water (100 mL). Wash the organic layer with saturated aqueous sodium chloride (4×30 mL) and dry over magnesium sulfate. Concentrate under reduced pressure to provide the desired compound (7.4 g, 56%).

MS (ES): m/z=229.1

N-[methoxy]-N-[methyl]3-cyclopentylamino-4-nitrobenzamide

Combine N-[methyl]N-[methoxy]3-fluoro-4-nitrobenzamide (2.3 g, 10 mmol), cyclopentylamine (12.3 mL, 100 mmol) and acetonitrile (50 mL) and stir at room temperature for 6 hours. Dilute with 1N HCl and extract with ethyl acetate. Wash the organic layer sequentially with water and saturated aqueous sodium chloride, then dry over magnesium sulfate. Concentrate under reduced pressure to provide the desired compound as an orange solid (2.7 g, 92%).

MS (ES): m/z=294.2.

N-[methoxy]-N-[methyl]3-cyclopentylamino-4-aminobenzamide

Combine N-[methoxy]-N-[methyl]3-cyclopentylamino-4-nitrobenzamide (2.0 g, 6.82 mmol), ammonium formate (2.1 g, 34.1 mmol), and 0.36 g (3.41 mmol) Pd(C) in ethanol (25 mL). Heat the mixture to 60° C. and stir for two hours. Cool to room temperature and filter through a pad of celite. Concentrate the filtrate under reduced pressure to provide the desired compound (1.79 g).

MS (ES): m/z=264.2

N-[methyl]-N-methoxy 1-(cyclopentyl)-2-amino-1H-benzimidazole-6-carboxamide

Combine N-[methoxy]-N-[methyl]3-cyclopentylamino-4-aminobenzamide (1.79 g, 6.82 mmol) and lithium methoxide (0.27 g, 7.16 mmol) in anhydrous dichloromethane (25 mL) and stir for 20 minutes. Add a solution of cyanogen bromide (0.83 g, 7.84 mmol) anhydrous dichloromethane (8 mL) and stir overnight at room temperature under nitrogen. Concentrate under reduced pressure and partition the residue between ethyl acetate and water. Wash the organic layer sequentially saturated aqueous sodium bicarbonate (2×20 mL), saturated aqueous sodium chloride (2×20 mL), and water (2×20 mL). Dry over magnesium sulfate and concentrate under reduced pressure to provide the desired compound as a dark solid (1.62 g, 82%).

MS (ES): m/e=289.2

Formation of Silyl Ether,

Add tert-butyllithium (1.7 M solution, 7.5 mL, 12.75 mmol) slowly to a solution of O-(tert-butyldimethyl)silyl benzyl alcohol (0.89 g, 3.11 mmol) in 60 mL of anhydrous tetrahydrofuran at −78° C. under a nitrogen atmosphere. Stir the solution for 3 hours, allowing the reaction to warm to −35° C. Add a solution of N-[methyl]N-[methoxy]1-(cyclopentyl)-2-aminobenzimidazole-6-carboxamide in 35 mL of anhydrous tetrahydrofuran. Stir the reaction for 2 hours while slowly warming to 0° C. Add saturated aqueous ammonium chloride and stir until mixture reaches room temperature. Dilute with ethyl acetate (100 mL). Wash the organic layer sequentially with aqueous ammonium chloride and water. Concentrate under reduced pressure. Subject the residue to silica gel chromatography, eluting with 1:1 dichloromethane:acetonitrile to provide 0.39 g (28%) of the title compound.

MS (ES): m/z=450.3

The compounds of Preparations 2 and 3 were prepared essentially as described in Preparation I:

| Prep. | Compound | MS (ESI⁻): m/z |
|---|---|---|
| 2 | 1-(2-Amino-1-phenyl-1H-benzimidazol-6-yl)-2-(tert-butyl-dimethylsilyl)oxy-2-(phenyl)ethan-1-one | 458.3 ($M^+ - H$) |
| 3 | 1-(2-Amino-1-(pent-3-yl)-1H-benzimidazol-6-yl)-2-(tert-butyldimethylsilyl)oxy-2-(phenyl)ethan-1-one | 452.3 ($M^+ - H$) |

Preparation 4

2,4-Diphenyl-5-(3-(isopropyl)amino-4-aminophenyl) imidazole

N-[Isopropyl]2-nitro-5-bromoaniline

Heat a mixture of 2,4-dibromonitrobenzene (3.50 g, 12.5 mmol), isopropylamine (4.42 g, 6.40 ml, 74.8 mmol) and n-butanol (20 ml) in a sealed reaction vessel to 117° C. overnight. Cool to room temperature and concentrate under reduced pressure. Partition the residue between ethyl acetate and saturated aqueous sodium chloride, dry the organic layer over sodium sulfate, and concentrate under reduced pressure to provide the desired compound as a yellow solid (3.0 g, 94%).
$^1$H-NMR (DMSO-d): δ7.96 (d, 1H, J=9.2 Hz), 7.87 (br, 1H), 7.26 (d, H, J=2.2 Hz), 6.82 (dd, 1H, J=2.2 and 9.2 Hz). 3.98 (m, 1H), 1.23 (d, 6H, J=6.1 Hz).

1-Phenyl-2-(3-(isopropyl)amino-4-nitrophenyl) acetylene

Bubble nitrogen through a mixture of N-[isopropyl]2-nitro-5-bromoaniline (0.34 g, 1.31 mmol), phenylacetylene (0.20 g, 1.96 mmol), palladium(II) acetate (7.3 mg, 0.033 mmol) and triphenylphosphine (17 mg, 0.065 mmol) in triethylamine (5 ml) for 3 minutes, then heat at reflux for 1 hour. Cool to room temperature and concentrate under reduced pressure. Partition the residue between ethyl acetate and saturated aqueous sodium chloride, dry the organic phase over sodium sulfate, and concentrate under reduced pressure. Subject the residue to silica gel chromatography, eluting with 9:1 hexane:ethyl acetate to provide the desired compound as a red solid (0.31 g, 85%).
$^1$H-NMR (DMSO-$d_6$), δ8.08 (d, 1H, J=8.8 Hz), 7.88 (br, d, 1H, J=7.5 Hz), 7.6 (m, 2H), 7.4 (m, 3H), 7.22 (d, 1H, J=1.3 Hz), 6.79 (dd, 1H, J=1.3 and 8.8 Hz).

1-Phenyl-2-(3-(isopropyl)amino-4-nitrophenyl) ethan-1,2-dione

Heat a mixture of 1-phenyl-2-(3-(isopropyl)amino-4-nitrophenyl)acetylene (0.10 g, 0.36 mmol) and palladium(II) chloride (6.3 mg, 0.036 mmol) in dimethylsulfoxide (3 ml) at 140° C. for 2 hours. Cool to room temperature and partition the reaction mixture between ethyl acetate and saturated aqueous sodium chloride. Wash the organic phase with saturated aqueous sodium chloride, dry over sodium sulfate and concentrate under reduced pressure. Subject the residue to silica gel chromatography, eluting with 9:1 hexane:ethyl acetate to provide the desired compound as an oil (0.055 g, 50%).
MS (ES): m/z=313.1

2,4-Diphenyl-5-(3-(isopropyl)amino-4-nitrophenyl) imidazole

Heat a mixture of 1-phenyl-2-(3-(isopropyl)amino-4-nitrophenyl)ethan-1,2-dione (0.10 g, 0.32 mmol), benzylaldehyde (0.96 mmol, 0.10 g) and ammonium acetate (0.099 g, 1.28 mmol) in acetic acid (3 ml) at 120° C. under nitrogen for 2 hours. Cool to room temperature and dilute with methanol (10 ml). Pass the reaction mixture through an SCX column, washing sequentially with methanol then 2N ammonia in methanol. Methanolic ammonia fractions are collected and concentrated under reduced pressure. The residue is subjected to silica gel chromatography, eluting with 1:1 dichloromethane:ethyl acetate to provide an oil. This oil is crystallized from methanol to provide the desired compound as a yellow solid (0.077 g, 60%).
$^1$H-NMR (DMSO-$d_6$): δ13.00 (br, 1H), 8.08-7.80 (m, 4H), 7.60-7.40 (m, 8H), 7.00 (m, 2H), 3.40 (m, 1H), 1.00 (m, 6H).

Reduction of Nitro Moiety

Stir a mixture of 2,4-diphenyl-5-(3-(isopropyl)amino-4-nitrophenyl)imidazole (0.077 g, 0.19 mmol) and 10% palladium on carbon (10 mg) in 5 mL each of methanol and ethyl acetate under a hydrogen atmosphere maintained with a balloon over night. Filter the reaction mixture and concentrate under reduced pressure to provide the title compound as a gray solid which is suitable for use without further purification.
$^1$H-NMR (DMSO-$d_6$): δ12.35 (br, 1H), 8.03 (d, 2H), 7.60-7.00 (ma, 8H), 6.60 (s, 2H), 6.40 (s, 1H), 3.40 (m, 1H), 1.05 (d, 6H).

Preparation 5

2-(2,6-Difluorophenyl)-4-phenyl-5-(3-(isobutyl) amino-4-aminophenyl)imidazole

Add ammonium formate (0.6 g, 9.6 mmol) followed by palladium on carbon (0.05 g, 0.48 mmol) to a solution of 2-(2,6-difluorophenyl-4-phenyl-5-(3-(isobutyl)amino-4-nitrophenyl)imidazole (1.0 g, 2.4 mmol) in 8 mL ethanol, and then heat the mixture to 60° C. for 3 hours. Cool the reaction mixture to room temperature, filter through celite, and concentrate the filtrate under reduced pressure to provide the title compound (0.99 g, 2.37 mmol)
MS (ES): m/z=419.4

Preparation 6

2-(2,6-Difluorophenyl)-4-phenyl-5-(3-(benzyl) amino-4-aminophenyl)imidazole

Add tin(II) chloride (0.11 g, 0.6 mmol) to a solution of 2-(2,6-difluorophenyl)-4-phenyl-5-(3-(benzyl)amino-4-nitrophenyl)imidazole (0.09 g, 0.2 mmol) in 10 mL acetic acid. Bubble nitrogen through the solution for 15 minutes and then heat at 90° C. for 1 hour under a nitrogen atmosphere. Cool the reaction mixture to room temperature, dilute with ethyl acetate, and then wash sequentially with 3:1 ammonium hydroxide:saturated aqueous ammonium chloride, saturated aqueous sodium chloride, and water. Dry the organic phase over magnesium sulfate and concentrate under reduced pressure. Subject the residue to silica gel chromatography, eluting with 5:1 dichloromethane:acetonitrile to provide the title compound (0.05 g, 59%).
MS (ES): m/z=453.1

The compounds of Preparations 7-15 may be prepared essentially as described in Preparation 4.

| Prep. | Compound | MS (ESI$^+$): m/z |
|---|---|---|
| 7 | 2-(2,6-Difluorophenyl)-4-phenyl-5-(3-(cyclopropylmethyl)-amino-4-aminophenyl)imidazole | 417.2 |
| 8 | 2-(2,6-Difluorophenyl)-4-phenyl-5-(3-(isopropyl)amino-4-aminophenyl)imidazole | 405.2 |
| 9 | 2-(4-(2-(Piperidin-1-yl)eth-1-oxy)phenyl)-4-phenyl-5-(3-(cyclopropylmethyl)amino-4-aminophenyl)imidazole | 508.3 |
| 10 | 2-(4-Chlorophenyl)-4-phenyl-5-(3-(cyclopropylmethyl)amino-4-aminophenyl)imidazole | 415.1 |
| 11 | 2-(2,6-Difluorophenyl)-4-phenyl-5-(3-(propyl)amino-4-aminophenyl)imidazole | 405.2 |
| 12 | 2-(2,6-Difluorophenyl)-4-Phenyl-5-(3-(methyl)amino-4-aminophenyl)imidazole | 377.4 |
| 13 | 2-(2,6-Difluorophenyl)-4-phenyl-5-(3-(ethyl)amino-4-aminophenyl)imidazole | 391.2 |
| 14 | 2-(2,6-Difluorophenyl)-4-phenyl-5-(3-(butyl)amino-4-aminophenyl)imidazole | 419.2 |
| 15 | 2-(2,6-Difluorophenyl)-4-phenyl-5-(3-(2,2-dimethylpropyl)-amino-4-aminophenyl)imidazole | 433.5 |

The compounds of Preparations 16-23 may be prepared essentially as described in Preparation 4, except that the nitro group reduction is performed essentially as described in Preparation 5.

| Prep. | Compound | MS (ESI$^+$): m/z |
|---|---|---|
| 16 | 2-(2,6-Difluorophenyl)-4-phenyl-5-(3-(benzyl)amino-4-aminophenyl)imidazole | 453.2 |
| 17 | 2-(2,6-Difluorophenyl)-4-phenyl-5-(3-(cyclohexylmethyl)-amino-4-aminophenyl)imidazole | 459.2 |
| 18 | 2-(tert-Butyl)-4-phenyl-5-(3-(isobutyl)amino-4-aminophenyl)imidazole | 363.3 |
| 19 | 2-(Isopropyl)-4-phenyl-5-(3-(isobutyl)amino-4-aminophenyl)imidazole | 349.3 |
| 20 | 2-(Trifluoromethyl)-4-phenyl-5-(3-(isobutyl)amino-4-aminophenyl)imidazole | 375.2 |
| 21 | 2-(Methyl)-4-phenyl-5-(3-(isobutyl)amino-4-aminophenyl)imidazole | 321.3 |
| 22 | 2-(2,6-Difluorophenyl)-4-phenyl-5-(3,4-diaminophenyl)imidazole | 363.1 |
| 23 | 2-(2-Chloro-6-fluorophenyl)-4-phenyl-5-(3-(isobutyl)amino-4-aminophenyl)imidazole | 435.4 |

Preparation 24

1-Cyclohexyl-4-phenyl-5-(3-(isobutylamino)-4-aminophenyl)-1H-imidazole

N-[Methyl]-N-[methoxy]-3-fluoro-4-nitrobenzamide

Add triethylamine (17 mL, 120 mmol) dropwise to a stirring solution of 3-fluoro-4-nitrobenzoic acid (17.8 g, 96 mmol), 1-(3-dimethylaminopropyl)-3-ethyl carbodiimide hydrochloride (23 g, 120 mmol), N,O-dimethylamine hydrochloride (11.25 g, 115.2 moles) and 4-N,N-dimethylaminopyridine (1.17 g, 9.6 mmol) in 300 mL dry dichloromethane under a nitrogen atmosphere. Stir at room temperature overnight. Add 10% hydrochloric acid (200 mL), dichloromethane (200 mL) and water (200 mL). Separate the phases and extract the aqueous phase twice with dichloromethane. Wash the combined organic phases sequentially with 10% aqueous hydrochloric acid, water, and saturated aqueous sodium chloride. Dry over magnesium sulfate and concentrate under reduced pressure to provide the desired compound (90%).

N-[Methyl]-N-[methoxy]-3-(isobutylamino)-4-nitrobenzamide

Add isobutylamine (8.7 mL) dropwise to a solution of N-[methyl]-N-[methoxy]-3-fluoro-4-nitrobenzamide (2 g, 8.77 mmol) in 80 mL dry acetonitrile at 0° C. Stir the resulting orange solution at room temperature over night. Concentrate under reduced pressure to provide the desired compound (90%).

MS (ES): m/z=282.1 (M$^+$+1).

3-(Isobutylamino)-4-nitrobenzaldehyde

Add lithium aluminum hydride (4.4 mL, 1 M in tetrahydrofuran) dropwise to a solution of N-[methyl]-N-[methoxy]-3-(isobutylamino)-4-nitrobenzamide (1.18 g, 4.2 mmol) in 20 mL of dry tetrahydrofuran at −78° C. Warm the mixture to −30° C. over 2 hours, and then to 0° C. over 30 minutes. Cool to −70° C. and carefully quench with 30 mL 5% aqueous potassium hydrogensulfate, warm to 0° C., and dilute with ethyl acetate. Separate the phases, dry the organic phase over magnesium sulfate and concentrate under reduced pressure to provide the desired benzaldehyde (70%).

N-[Cyclohexyl]3-(isobutylamino)-4-nitrobenzaldimine

Stir a mixture of 3-(isobutylamino)-4-nitrobenzaldehyde (656 mg, 2.95 mmol) and cyclohexylamine (0.44 mL, 3.84 mmol) in 5 mL dimethylformamide at room temperature over night. Dilute the reaction mixture with ethyl acetate and wash sequentially with water and saturated aqueous sodium chloride. Dry the organic phase over sodium sulfate and concentrate under reduced pressure to provide the desired compound (78%).

1-Cyclohexyl-4-phenyl-5-(3-(isobutylamino)-4-nitrophenyl)-1H-imidazole

Heat a solution of N-[cyclohexyl]3-(isobutylamino)-4-nitrobenzaldimine (700 mg, 2.29 mmol), α-(p-toluenesulfonyl)benzylisocyanide (1 g), and cyclohexylamine (0.65 mL, 5.72 mmol) in 15 mL methanol at 65° C. over night. Cool to room temperature and concentrate under reduced pressure. Subject the residue to silica gel chromatography, eluting with 6:1 dichloromethane:acetonitrile to provide the desired compound (74%).

MS (ES): m/x=419.2 (M$^+$+1).

Reduction of Nitro Group

Beginning with 1-cyclohexylphenyl-5-(3-(isobutylamino)-4-nitrophenyl)-1H-imidazole (670 mg, 1.60 mmol), the title compound was prepared essentially as described in Preparation 5 (98%).

MS (ES): m/z=389.2 (M$^+$+1).

Preparation 25

α-(p-Toluenesulfonyl)benzylisocyanide

N-[Formyl]α-(p-toluenesulfonyl)benzylamine

Method A.

Add concentrated hydrochloric acid (3 mL) dropwise to a solution of p-toluene-sulfinic acid sodium salt in water (20 mL) and tert-butyl methyl ether (10 mL). Stir for 10 minutes and then separate the layers. Wash the organic layer with saturated aqueous sodium chloride, dry over sodium sulfate and concentrate under reduced pressure to provide 5 g of p-toluenesulfinic acid. Combine this acid with benzaldehyde (4.75 g, 44.8 mmol), formamide (4.9 g, 0.11 mol), and camphorsulfonic acid (0.86 g, 3.7 mmol) and heat to 60° C. for 18 hours. Remove the reaction from the heat and slurry the white solid in 3:1 hexanes:methanol. Filter the slurry to provide 7.6 g (82%) of the desired product as a white solid.

$^1$H-NMR (DMSO-$d_6$): §9.75 (d, 1H), 7.98 (s, 1H), 7.69 (d, 2-1), 7.53 (d, 21, 7.39 (m, 5H), 6.36 (d, 1H), 2.38 (s, 1H).

Method B.

Treat a solution of p-toluenesulfinic acid sodium salt, (6.0 g, 33.7 mmol) in water (20 mL) and tert-butyl methyl ether (10 mL) dropwise with concentrated HCl (3 mL) and stir for 10 minutes. Separate the solution in a separatory funnel and wash the organic layer with saturated aqueous sodium chloride. Dry the organic over $Na_2SO_4$, filter, and remove the solvent to afford 5.2 g (quantitative) of p-toluenesulfinic acid. Combine the acid with benzaldehyde (2.4 g, 22.5 mmol), formamide (3.8 g, 84.2 mmol), and trimethylsilyl chloride (4.0 g, 37.0 mmol) in 30 mL of a 1:1 solution of toluene/acetonitrile. Heat the reaction to 50° C. and stir for 5 hours. Cool the reaction and dilute with water (100 mL) and tert-butyl methyl ether (30 mL). Cool the solution in an ice bath and filter to afford 4.5 g (70%) of desired product. Dry the solid under vacuum overnight to remove any residual water.

$^1$H-NMR (DMSO): 9.75 (d, 1H), 7.98 (s, 1H), 7.69 (d, 2H), 7.53 (d, 2H), 7.39 (m, 5H), 6.36 (d, 1H), 2.38 (s, 1H).

Dehydration

Cool a solution of N-[formyl]α-(p-toluenesulfonyl)benzylamine (7.0 g, 0.024 mol) in dimethoxyethane (200 mL) to −10° C. Add phosphorus oxychloride (5.6 mL, 0.06 mol) followed by the dropwise addition of triethylamine (16.8 mL, 0.12 mol) in dimethoxyethane (10 mL) maintaining a reaction temperature below −5° C. Warm the reaction mixture gradually over 1 hour, add water and extract with ethyl acetate. Separate the layers, wash the organic phase with saturated aqueous sodium bicarbonate, dry over sodium sulfate, and concentrate under reduced pressure to provide 6.5 g of the title compound.

MS (ES$^-$): m/z=270.1 (M−H)$^-$

Preparation 26

(1-Isobutyl-2-aminobenzimidazol-6-yl)boronic acid

1-Isobutyl-6-bromo-2-aminobenzimidazole

Add tin(II) chloride dihydrate (245.5 g, 1.09 mol) to a solution of N-[isobutyl]2-nitro-5-bromoaniline (49.5 g, 0.180 mol) in 2:1 ethyl acetate:ethanol (900 mL). Stir at 70° C. for 2 hours. Pour the reaction mixture into a slurry of ice in water and treat with saturated aqueous sodium bicarbonate. Add ethyl acetate (250 mL) and wash the organic phase sequentially with water (2×600 mL) and saturated aqueous sodium chloride (2×600 mL). Dry over magnesium sulfate and concentrate under reduced pressure. Dissolve the residue in ethanol (600 mL). Add cyanogen bromide (32.6 g, 0.31 mol) and stir at room temperature for 15 hours. Add saturated aqueous sodium carbonate (500 mL) and extract with ethyl acetate (600 mL). Wash the organic phase sequentially with water (2×400 mL) and saturated aqueous sodium chloride (2×400 mL). Dry over magnesium sulfate and concentrate under reduced pressure. Suspend the residue in diethyl ether (300 mL), stir for 15 minutes, filter, and dried under reduced pressure to provide the desired compound as a light brown solid (41.7 g, 86% yield).

MS (ES): m/z=268.1 (M+H)//270.1 (M+H+2 $^{81}$Br).

Formation of Boronic Acid

Add phenyllithium (1.8M, 102.6 mL, 184.7 mmol) to a solution of 1-isobutyl-6-bromo-2-aminobenzimidazole (15.0 g, 55.9 mmol) in tetrahydrofuran (300 mL) at −78° C. Stir for 15 minutes and then add tert-butyllithium (1.7M, 101.9 mL, 173.3 mmol). Stir for 3 hours, allowing temperature to rise to −30° C. Add triisopropyl borate (38.9 mL, 167.7 mmol) and stir for 1 hour. Add saturated aqueous ammonium chloride and then extract with ethyl acetate:methanol (99:1, 300 mL). Wash the organic phase sequentially with water (2×300 mL) and saturated aqueous sodium chloride (2×300 mL). Dry over magnesium sulfate and concentrate under reduced pressure. Suspend the residue in ethyl acetate (150 mL), stir for 15 hours, filter, and dry under reduced pressure to provide the title compound as a white solid (11.3 g, 87% yield).

MS (ES): m/z=234.2 (M+H).

Preparation 27

3-Bromo-2-phenyl-6,7-dihydro-5H-pyrrolo[1,2-a]imidazole

2-Phenyl-6,7-dihydro-5H-pyrrolo[1,2-a]imidazole

Combine 2-iminopyrrolidine hydrochloride (6.98 g, 57.8 mmol) (Callahan, et al., *J. Med. Chem.* 45, 999-1001 (2002)), 2-bromoacetophenone (3.8 g, 19.3 mmol), and sodium carbonate (8.2 g, 77.2 mmol) in dry dimethylformamide (25 mL). Heat at 80° C. for 18 hours. Cool to room temperature, add water (60 mL), and extract with ethyl acetate (3×100 mL). Concentrate the combined organic layers under reduced pressure. Dilute the residue with diethyl ether (100 mL), wash with cold water (3×80 mL), and concentrate under reduced pressure to provide the desired compound as a white solid (3.2 g, 89%).

MS (ES): m/z=185.1 (M$^+$+H)

Bromination

Add bromine (1.0 mL, 20.2 mmol) to a solution of 2-phenyl-6,7-dihydro-5H-pyrrolo[1,2-a]imidazole (3.38 g, 18.3 mmol) in dry dichloromethane (113 mL). Stir at room temperature for 1.5 hours. Add saturated aqueous sodium bicarbonate (100 mL) and extract with dichloromethane (3×100 mL). Wash the combined organic layers with sodium hydrogen sulfite (40%, 30 mL), dry over magnesium sulfate, and concentrate under reduced pressure. Subject the residue to silica gel chromatography, eluting with a gradient of dichloromethane containing from 0-5% methanol to provide the title compound as a red solid (3.54 g, 73%).

MS (ES): m/z=263.0 (M$^+$+H)

Preparation 28

3-Bromo-2-(4-fluorophenyl)-6,7-dihydro-5H-pyrrolo[1,2-a]imidazole

Beginning with 2-fluoroacetophenone, the title compound is prepared essentially as described in Preparation 27.

Preparation 29

1-(3-(Isobutylamino)-4-aminophenyl)-2-phenyl-1H-imidazole

N-(Isobutyl)-2-nitro-5-fluoroanline

Add potassium carbonate (26.9 g, 195 mmol) and isobutylamine (19.4 mL, 195 mmol) to a solution of 2,4-difluoronitrobenzene (31.0 g, 195 mmol) in 200 mL of anhydrous tetrahydrofuran at 0° C. Stir at room temperature over night Filter reaction mixture and wash solid with ethyl acetate. Concentrate filtrate under reduced pressure to provide the desired compound as a yellow-orange oil (41.3 g, 99%).

MS (ES): m/z=213.0 (M$^+$+1)

1-(3-(Isobutylamino)-4-nitrophenyl)-2-phenyl-1H-imidazole

Add sodium hydride (60% oil dispersion, 94 mg, 2.36 mmol) to a solution of 2-phenylimidazole (340 mg, 2.36 mmol) in 8 mL dimethylformamide. Stir at room temperature for 15 minutes and then add N-[isobutyl]2-nitro-5-fluoroaniline (500 mg, 2.36 mmol). Stir at 60° C. over night under a nitrogen atmosphere. Dilute the reaction mixture with ethyl acetate and wash with dilute aqueous sodium bicarbonate. Dry the organic phase over sodium sulfate, filter, and concentrate under reduced pressure. Subject the residue to radial silica gel chromatography, eluting with a gradient of 0.1%-5% methanol in dichloromethane to provide the desired compound as a yellow solid (450 mg, 57%).

MS (ES): m/z=337.0 (M$^+$+1)

Reduction

Add Raney Nickel (45 mg) to a solution of 1-(3-(isobutylamino)-4-nitrophenyl)-2-phenyl-1H-imidazole (450 mg, 1.34 mmol) in 70 mL tetrahydrofuran. Stir the mixture at room temperature over night under a hydrogen atmosphere (60 psi). Filter the reaction mixture and concentrate the filtrate under reduced pressure to provide the title compound as a yellow oil.

MS (ES): m/z=307.0 (M$^+$+1)

Preparation 30

3-Phenyl-4-(3-(isobutylamino)-4-aminophenyl)-1H-pyrazole 2-(3-Isobutylamino)-4-nitrophenyl)acetophenone Add a solution of 1-phenyl-2-(3-(isobutylamino)-4-nitrophenyl)acetylene (1.5 g, 5.06 mmol) in 50 mL methanol to a solution of mercuric oxide (HgO) in aqueous sulfuric acid (38 mL of a solution of 312 mg of HgO in 50 mL of 4% w/v sulfuric acid) in a sealed tube. Heat at 100° C. over night. Cool to room temperature. Quench carefully with saturated aqueous sodium bicarbonate. Extract well with dichloromethane. Wash combined organic phases with saturated aqueous sodium chloride, dry over magnesium sulfate and concentrate under reduced pressure. Subject the residue to silica gel chromatography, eluting with a gradient of dichloromethane containing 5-8% methanol to provide the desired compound (70%).

MS (ES): m/e=313.1 (M$^+$+1).

3-Phenyl-4-(2-(isobutylamino)-3-nitrophenyl-1H-pyrazole

Add dimethylformamide-dimethylacetal (0.38 mL, 2.86 mmol) to a stirred solution of 2-(3-(isobutylamino)-4-nitrophenyl)acetophenone (180 mg, 0.57 mmol in 0.6 mL of dry dimethylformamide. Heat at 80° C. for 1.5 hours. Cool to room temperature and concentrate under reduced pressure. Dissolve the residue in ethanol (3 mL). Add hydrazine (0.2 mL) dropwise. Stir at room temperature over night. Concentrate under reduced pressure. Subject the residue to silica gel chromatography, eluting with dichloromethane containing 5% methanol to provide the desired compound (76%).

MS (ES): m/z=337.1 (M$^+$++1).

Reduction

Add 10% palladium on carbon (100 mol %) to a stirred suspension of 3-phenyl-4-(2-(isobutylamino)-3-nitrophenyl)-1H-pyrazole (143 mg, 0.42 mmol) in ethanol (4 mL). Bubble hydrogen through the suspension for 5 minutes. Stir the mixture for 2 hours under a hydrogen atmosphere (1 atm). Filter through celite. Rinse filter cake well with 10% methanol in dichloromethane. Concentrate filtrate under reduced pressure. Subject the residue to silica gel chromatography, eluting with 5% methanol in dichloromethane to provide the title compound (81%).

MS (ES): m/z=307.1 (M$^+$+1).

Preparation 31

4-Phenyl-5-(3-(isopropylamino)-4-aminophenyl)-[1,2,3]triazole

4-Phenyl-5-(3-(isopropylamino)-4-nitrophenyl)-[1,2,3]triazole

Add sodium azide (0.13 g) to a solution of 1-phenyl-2-(3-(isopropylamino)-4-nitrophenyl)acetylene (0.56 g) in dimethoxyethane (5 mL). Heat to reflux for 2 hours. Cool to room temperature. Add 1N hydrochloric acid (10 mL), extract with ethyl acetate (20 mL), and wash with saturated aqueous sodium chloride (2×10 mL). Dry organic phase over sodium sulfate and concentrate under reduced pressure. Subject the reside to silica gel chromatography, eluting with 1:1 ethyl acetate:hexane to provide the desired compound as a yellow solid (0.51 g, 80%).

MS (ES): m/z=326.27 (M$^+$+H).

Reduction

Beginning with 4-phenyl-5-(3-(isopropylamino)-4-nitrophenyl)-[1,2,3]triazole (0.25 g), the title compound (0.21 g, 95%) is prepared essentially as described in Preparation 5.

MS (ES): m/z=294.37 (M$^+$+H).

Preparation 32

2-(2-Chloro-6-fluorophenyl)-4-phenyl-5-(3-amino-4-(isobutylamino)phenyl)-1H-imidazole 1-Phenyl-2-(3-nitro-4-(isobutylamino)phenyl)acetylene Beginning with 2-fluoro-5-bromonitrobenzene and isobutylamine, the desired compound was prepared essentially as described in Preparation 4.

MS (ES): m/z=295.14 (M$^+$+H).

1-Phenyl-2-(3-nitro-4-(isobutylamino)phenyl)ethane-1,2-dione

Add potassium permanganate (2.49 g) to a mixture of 1-phenyl-2-(3-nitro-4-(isobutylamino)phenyl)acetylene (1.17 g), sodium bicarbonate (0.20 g), and magnesium sulfate (0.98 g), in water (5 mL) and acetone (5 mL). Stir at room temperature over night. Pour into saturated aqueous sodium sulfite, extract with ethyl acetate, dry over sodium sulfate, and concentrate under reduced pressure to provide the title compound as a red solid (0.89 g, 69%).

MS (ES): m/z=327.13 (M$^+$+H).

2-(2-Chloro-6-fluorophenyl)-4-phenyl-5-(3-nitro-4-(isobutylamino)phenyl)-1H-imidazole Beginning with 1-phenyl-2-(3-nitro-4-(isobutylamino)phenyl)ethane-1,2-dione (0.80 g) and 2-fluoro-6-chlorobenzaldehyde, the desired compound (0.90 g, 82%) is prepared essentially as described in Preparation 4.

MS (ES): m/z=465.37 (M$^+$+H).

Reduction

Beginning with 2-(2-chloro-6-fluorophenyl)-4-phenyl-5-(3-nitro-4-(isobutyl-amino)phenyl)-1H-imidazole (0.46 g), the title compound is prepared (0.149 g, 55%) essentially as described in Preparation 6.

MS (ES): m/z=465.37 (M$^+$+H).

Preparation 33

N-[Cyano]N-[isobutyl]2-nitro-5-(5,5-dimethyl-[1,3,2]dioxaborinan-2-yl)aniline

N-[Isobutyl]2-nitro-5-chloroaniline

Add a solution of isobutylamine (14 mL, 0.138 mol), potassium carbonate (10.4 g, 0.075 mol) and water (50 mL) to a solution of 4-chloro-2-fluoro-nitrobenzene (11.0 g, 0.063 mol) in tetrahydrofuran (0.3 L) and stir at ambient temperature for 3 hours. Separate phases and wash organic layer with 1:1 solution of 1N HCl (aq)/saturated sodium chloride. Dry organic phase with solid magnesium sulfate, filter and concentrate under reduced pressure to give 14.5 g (0.063 mol) of the desired compound as an orange oil that solidifies upon standing.

MS (ES+H): m/z=229.2.

N-[Cyano]-[isobutyl]2-nitro-5-chloroaniline

Add lithium bis(trimethylsilyl)amide (45 mL, 1M in tetrahydrofuran) to a solution of N-[isobutyl]2-nitro-5-chloroaniline (5.2 g, 0.0226 mol) in tetrahydrofuran (50 mL) cooled in an ice bathe Stir for 30 minutes and add cyanogen bromide (5.3 g, 0.050 mol). Stir at room temperature for 3 hours. Concentrate under reduced pressure. Dissolve residue in dichloromethane, wash saturated aqueous sodium chloride, dry over magnesium sulfate, filter, and concentrate under reduced pressure. Subject residue to silica gel chromatography, eluting with hexane/ethyl acetate mixtures to provide 5.26 g (0.021 mol) of desired compound.

MS (ES+H): m/z=254.0.

Coupling

Heat a mixture of N-[cyano]N-[isobutyl]2-nitro-5-chloroaniline (5.1 g, 20.3 mmol), bis(neopentyl glycoloto)-diboron (7.8 g, 34 mmol), palladium(II)acetate (0.45 g, 2 mmol), tricyclohexylphosphine (1.14 g, 4 mmol), cesium fluoride (27.7 g, 182 mmol) and acetonitrile (100 mL) to reflux for 20 minutes. Cool to room temperature, filter, and concentrate under reduced pressure. Partition residue between dichloromethane and water. Wash organic phase with saturated aqueous sodium chloride, dry over solid magnesium sulfate, filter, and subject to silica gel chromatography, eluting with hexane/dichloromethane mixtures to give 3.3 g (9.9 mmol) of the title compound. MS (ES+H): m/z=332.1.

Preparation 34

1-Benzyl-2-methyl-4-bromo-5-(2,4-difluorophenyl)-1H-imidazole

1-Benzyl-2-methyl-5-bromo-1H-imidazole

Add N-bromosuccinimide (7.85 g, 44 mmol) to a solution of 1-benzyl-2-methyl-1H-imidazole (8.0 g, 46 mmol) in chloroform (200 mL) and stir for 6 hours. Wash reaction with saturated aqueous sodium hydrogen carbonate and saturated aqueous sodium chloride, dry over magnesium sulfate, and filter through 2" pad of silica gel. Concentrate filtrate reduced pressure. Suspend residue in diethyl ether (600 mL), heat to reflux and filter hot Concentrate ether filtrate under reduced pressure to give 9.3 g (37 mmol) of the desired compound as a tan solid.

MS (ES+H): m/z=250.8/252.8.

1-Benzyl-2-methyl-5-(2,4-difluorophenyl)-1H-imidazole

Heat a mixture of 1-benzyl-2-methyl-5-bromo-1H-imidazole (4.71 g, 18.7 mmol), 2,4-difluorophenyl boronic acid (6.92 g, 43.8 mmol), bis(acetato)bis(triphenylphosphine)palladium(II) (1.4 g, 1.875 mmol), 2M sodium carbonate (19 mL, 38 mmol), methanol (19 mL) and 1,2-dimethoxyethane (120 mL) to reflux for 18 hours. Cool to room temperature. Add water and ethyl acetate and separate layers. Dry organic layer over magnesium sulfate, filter, and concentrate under reduced pressure. Subject residue to silica gel chromatography, eluting with ethyl acetate/dichloromethane mixtures to give 3.59 g (12.6 mmol) of the desired compound.

MS (ES+H): m/z=285.0.

Bromination

Stir a mixture of 1-benzyl-2-methyl-5-(2,4-difluoro-phenyl)-1H-imidazole (3.58 g, 12.6 mmol), N-bromosuccinimide (2.24 g, 12.6 mmol), and chloroform (100 mL) at room temperature for 18 hours. Charge reaction mixture directly onto silica gel and elute with dichloromethane/ethyl acetate mixtures to give 3.41 g (9.4 mmol) of the title compound.

MS (ES+H): m/z=363.0/364.9.

Preparation 35

1-Benzyl-2-methyl-4-(3-(N-[isobutyl]-N-[cyano]amino)-4-nitrophenyl)-5-(2,4-difluorophenyl)-1H-imidazole Heat 1-benzyl-2-methyl bromo-5-(2,4-difluorophenyl)-1H-imidazole (0.321 g, 0.885 mmol), N-[cyano]N-[isobutyl]2-nitro-5-(5,5-dimethyl-[1,3,2]dioxaborinan-2-yl)aniline (0.352 g, 1.06 mmol), palladium(II)acetate (0.0099 g, 0.044 mmol), di-tert-butylphosphinoferrocene (0.058 g, 0.177 mmol), and potassium carbonate (0.45 g, 3.26 mmol) in dioxane (10 mL) to 100° C. for 20 hours. Cool to room temperature and concentrate under reduced pressure. Subject residue to silica gel chromatography, eluting with dichloromethane/ethyl acetate mixtures to provide 0.191 g (0.38 mmol) of the title compound.

MS (ES+H): m/z=502.1.

Preparation 36

1-Benzyl-2-methyl-4-(3-(N-[3-methylbut-2-yl]-N-[cyano]amino)-4-nitrophenyl)-5-(2,4-difluorophenyl)-1H-imidazole Beginning with 1-benzyl-2-methyl-4-bromo-5-(2,4-difluorophenyl)-1H-imidazole and N-[cyano]N-[3-methylbut-2-yl]2-nitro-5-(5,5-dimethyl-[1,3,2]dioxaborinan-2-yl) aniline, the title compound is prepared essentially as described in Preparation 35.
MS (ES+H): m/z=516.2.

Preparation 37

1-Benzyl-2-methyl-4-(3-(N-[isobutyl]]amino)-4-nitrophenyl)-5-(2,4-difluorophenyl)-1H-imidazole Beginning with 1-benzyl-2-methyl-4-bromo-5-(2,4-difluorophenyl)-1H-imidazole and N-[isobutyl]2-nitro-5-(5,5-dimethyl-[1,3,2]dioxaborinan-2-yl)aniline, the title compound is prepared essentially as described in Preparation 35.
MS (ES+H): m/z=477.2.

Preparation 38

1-Isobutyl-2-amino-6-formylbenzimidazole

Add phenyllithium (19.4 mL, 33 mmol, 1.7M in cyclohexane/diethyl ether) dropwise over 20 minutes to a solution of 1-isobutyl-2-amino-6-bromobenzimidazole (2.68 g, 10 mmol) in tetrahydrofuran (50 mL) at −78° C. Stir 40 minutes after addition is complete and then add tert-butyllithium (17.6 mL, 30 mmol, 1.7M in pentane) dropwise over 20 minutes. Stir 1.5 hours after addition is complete and then add dimethylformamide (5 mL) dropwise over 5 minutes. Warm reaction mixture to 0° C. over 1 hour, and then to room temperature over 20 minutes. Dilute reaction mixture with saturated aqueous ammonium chloride (100 mL), and then extract well with ethyl acetate. Combine ethyl acetate extracts, wash sequentially with water and saturated aqueous sodium chloride, dry over sodium sulfate and concentrate under reduced pressure. Slurry the residue in diethyl ether, filter and dry to provide 1.58 g of the title compound.
MS (ES): m/z=218.2 (M$^+$+1).

Preparation 39

6-Phenylethynyl-1-(1-(R)-methyl-2,2-dimethylpropyl)-1H-benzimidazol-2-ylamine (5-Chloro-2-nitrophenyl)-(1-(R)-methyl-2,2-dimethylpropyl)amine Add 2-(R)-amino-3,3-dimethylbutane (20 mL, 0.148 mol), potassium carbonate (14.3 g, 0.104 mol) and water (50 mL) to a solution of 4-chloro-2-fluoronitrobenzene (13.3 g, 0.076 mol) in THF (450 mL) and stir at 75° C. for 3 h Cool to ambient temperature. Concentrate to ½ volume, dilute with ethyl acetate and wash with 1N HCl (4×100 mL), water, saturated sodium bicarbonate, saturated sodium chloride, dry with magnesium sulfate and concentrate to give the title compound as an orange solid (19.6 g, quant).
MS (ES+H): m/z=257.1.

4-Phenylethynyl-N$^2$-(1-(R)-methyl-2,2-dimethylpropyl)benzene-1,2-diamine

Stir (5-Chloro-2-nitrophenyl)-(1-(R)-methyl-2,2-dimethylpropyl)amine (17.23 g, 0.067 mol), copper (I) iodide (0.64 g, 0.0034 mol), (oxydi-2,1-phenylene)bis(diphenylphosphine) (3.61 g, 0.0067 mol), phenylacetylene (12.5 mL, 0.114 mol) in DMF (200 mL) and diethylamine (50 mL) for 5 minutes. Add palladium (II) acetate (0.753 g, 0.0034 mol) and heat to 95° C. for 4 h. Cool to ambient temperature and evaporate off diethylamine under reduced pressure and pour into hexane. Filter insolubles and evaporate off hexane. Dilute with ethyl ether (1 L), filter and wash filtrate with water (2×1 L), saturated sodium chloride, dry magnesium sulfate, concentrate and purify (silica gel chromatography eluting with hexane/dichloromethane mixtures) to give 27.9 g of crude (2-nitro-5-phenylethynylphenyl)-(1-(R)-methyl-2,2-dimethylpropyl)amine that was used in the next step without further purification. To a solution of impure (2-nitro-5-phenylethynylphenyl)-(1-(R)-methyl-2,2-dimethylpropyl) amine (27.9 g) in THF (350 mL), water (100 mL), concentrated ammonium hydroxide (150 mL), Na$_2$S$_2$O$_4$ (73.6 g, 0.423 mol) and stir for about 18 hours. Dilute with ethyl acetate and wash with saturated sodium chloride, dry with magnesium sulfate, concentrate and purify (silica gel chromatography with hexane/dichloromethane mixtures to give 14.51 g of the desired compound (75% for 2 Steps).
MS (ES+H): m/z=293.2

Cyclization

Add cyanogen bromide (7.88 g, 0.074 mol) to a solution of 4-phenylethynyl-N$^2$-(1-(R)-methyl-2,2-dimethylpropyl) benzene-1,2-diamine in absolute ethanol (500 mL) and stir 4.5 h. Concentrate and redissolve in dichloromethane, wash with saturated sodium bicarbonate and purify (silica gel chromatography with dichloromethane/methanol mixtures to give 16.9 g (quant) of the title compound as a tan solid.
MS (ES+H): m/z=318.2.

Preparation 40

6-Phenylethynyl-1-(1-(S)-methyl-2,2-dimethylpropyl)-1H-benzimidazol-2-ylamine

Beginning with 2-(S)-amino-3,3-dimethylbutane (13.3 g), the title compound is prepared essentially as described in Preparation 39 (2.74 g).
MS (ES): m/z=318.2 (M$^+$+1).

Preparation 41

N-[6-(2-Oxo-2-phenylacetyl)-1-(1-(R)-methyl-2,2-dimethylpropyl)-1H-benzimidazol-2-yl]acetamide N-[6-Phenylethynyl-1-(1-(R)-methyl-2,2-dimethylpropyl)-1H-benzimidazol-2-yl]acetamide Add 6-phenylethynyl-1-(1-(R)-methyl-2,2-dimethylpropyl)-1H-benzimidazol-2-ylamine (5.81 g, 0.018 mol), triethylamine (12 mL), dichloromethane (100 mL), N,N-dimethylaminopyridine (0.11 g, 0.9 mmol), and acetic anhydride (7.5 mL) and stir for about 18 hours. Evaporate and redissolve in ethyl acetate and wash with water, 1N HCl (3×), saturated sodium bicarbonate, and saturated sodium chloride. Add 2M ammonia in methanol to organic layer and stir 10 minutes and evaporate. Redissolve in dichloromethane and wash with saturated sodium bicarbonate, saturated sodium chloride, dry magnesium sulfate, and concentrate to give the desired compound as an orange foam (6.92 g, quant).

MS (ES): m/z=360.2 (M++H).

Oxidation

Add N-[6-phenylethynyl-1-(1-(R)-methyl-2,2-dimethylpropyl)-1H-benzimidazol-2-yl]acetamide (6.92 g, 0.019 mol) and $PdCl_2$ (0.34 g) in DMSO (30 mL) and heat to 140° C. for about 18 hours, then cool to ambient temperature. Add water (170 mL) and filter through Celite. Wash cake with water and dry for about 18 hours. Dissolve cake in dichloromethane and filter through a silica gel pad, wash with dichloromethane and evaporate to give the title compound (4.82 g 64%).

MS (ES): m/z=392.2 (M++H).

Preparation 42

4-Bromo-3-(4-fluorophenyl)-1-methyl-1H-pyrazole 3-(4-Fluorophenyl-1-methyl-1H-pyrazole Treat a solution of 3-(4-fluorophenyl)pyrazole (7.17 g, 44.2 mmol) in dry DMF (60 mL) with NaH (2.2 g, 92.8 mmol) at 0° C. for 15 min. Add iodomethane (3.3 mL, 53.04 mmol) and slowly warm to RT. Quench the reaction mixture with methanol (5 mL) and dilute with water (100 mL). Extract with EtOAc (3×70 mL), dry ($MgSO_4$) and concentrate and purify (Biotage system eluting with dichloromethane:methanol 50:1) to give desired compound as a white solid (2.3 g, 29% yield).

MS (ESi+): 177 (M+H)+.

Bromination

Prepare the desired compound in a manner essentially as described as Preparation 28 using 3-(4-fluorophenyl)-1-methyl-1H-pyrazole (3.0 g, 94% yield).

MS (ESi+): 254.9 (M+H)+, 257.0 (M+H+2)+.

Preparation 43

4-Bromo-3-(4-fluorophenyl)-1-tert-butyl-1H-pyrazole

4-Ethoxycarbonyl-3-(4-fluoro-phenyl)-1-tert-butyl-1H-pyrazole

Add dropwise a solution of N-tert-butyl-N'-(4-fluorobenzylidene)hydrazine (*Tetrahedron*, 1986, 42, 4223-4234) (8.4 g, 43.2 mmol) in acetonitrile (43 mL) to a well stirred mixture of ethyl propiolate (4.4 mL, 43.2 mmol) and acetic acid (37 mL, 648 mmol) at RT. Warm the mixture at 50° C. for 2 days and at 60° C. for 1 day. Cool at RT and dilute with dichloromethane (250 mL). Wash the mixture with water (50 mL), a saturated aqueous solution of $Na_2CO_3$ (2×50 mL), dry ($MgSO_4$), concentrate and purify (Biotage system eluting with $CH_2Cl_2$). Dissolve the yellow solid obtained in dichloromethane (43 mL) and acetic acid (37 mL) and bubble a stream of $O_2$ at RT for 10 days. Dilute the mixture with dichloromethane (100 mL) and wash with a saturated aqueous solution of $Na_2CO_3$ (2×50 mL), dry ($MgSO_4$) and concentrate and purify (Biotage system eluting with $CH_2Cl_2$) to provide the desired compound as yellow solid (6.4 g, 51% yield).

MS (ESi+): 291 (M+H)+.

Decarboxylation and Bromination

Add a solution of NaOH (15%, 6 mL) to a solution of 4-ethoxycarbonyl-3-(4-fluorophenyl)-1-tert-butyl-1H-pyrazole (0.350 g, 1.2 mmol) in MeOH (3 mL) and then add acetonitrile (1 mL). Stir the mixture at 50° C. for 3 h, cool to RT and add HCl (10%) until the pH=3. Extract the mixture with EtOAc (3×100 mL). Combine the organic layers and wash with brine (100 mL), dry ($MgSO_4$) and concentrate to provide 4-carboxy-3-(4-fluorophenyl)-1-tert-butyl-1H-pyrazole as a yellow solid (0.320 g), MS (ESi+): 229.1 (M+H)+. Next treat a solution of 4-carboxy-3-(4-fluorophenyl)-1-tert-butyl-1H-pyrazole (0.315 g, 1.2 mmol) in DMF (15 mL) previously degassed with N-bromosuccinimide (0.235 g, 1.32 mmol) at RT for about 18 h. Dilute the mixture with EtOAc (80 mL) and wash with cooled water (5×10 mL), dry ($MgSO_4$), and concentrate to provide the desired compound as yellow solid (0.262 g, 73% yield).

MS (ESi+): 297 (M+H)+, 299 (M+H+2)+.

Preparation 44

1-Trityl-3-(2,4-difluorophenyl)-4-(1-(isobutyl)-2-aminobenzimidazol-6-yl)pyrazole 3-(2,4-Difluorophenyl)-1H-pyrazole Add N—N-dimethylformamide dimethyl acetal (4.57 mL, 34.44 mmol) to a stirred solution of 1-(2,4-difluorophenyl) ethanone (4 mL, 31.60 mmol). Stir at 120° C. for 18 hours. Cool to RT and concentrate. Dissolve the residue in ethanol (30 mL). Add hydrazine hydrate (2 mL) drop wise. Stir at RT for about 8 hours. Concentrate and purify (silica gel chromatography, eluting with dichloromethane:methanol 95:05) to give the desired compound (85%).

MS (ES): m/z=179.1 (M+−1).

3-(2,4-Difluorophenyl)-1-trityl-1H-pyrazole

Add triphenylmethylchloride (4.78 g, 17.2 mmol)) and dimethylaminopyridine (0.350 g, 2.86 mmol) to a stirred solution of 3-(2,4-difluorophenyl)-1H-pyrazole (2.58 g, 14.33 mmol) in dry pyridine (30 mL). Stir at 80° C. for about 18 hours. Cool to RT, concentrate and purify (silica gel chromatography, eluting with a gradient of hexane dichloromethane 25:75 to 0:100) to give the desired compound (43%).

MS (ES): m/z=423.1 (M++1).

4-Bromo-3-(2,4-difluorophenyl)-1-trityl-1H-pyrazole

Beginning with 3-(2,4-difluorophenyl)-1-trityl-1H-pyrazole the desired compound is prepared essentially as described in Preparation 27. $^1$HNMR ($CDCl_3$): δ 6.87 (m, 2H), 7.17 (m, 6H), 7.32 (m, 9H), 7.42 (s, 1H), 7.43 (m, 1H).

Coupling

Beginning with 4-bromo-3-(2,4-difluorophenyl)-1-trityl-1H-pyrazole and (1-isobutyl-2-aminobenzimidazol-6-yl)boronic acid, the desired compound is prepared essentially as described in Preparation 34 (69%).

MS (ES): m/z=610.3 (M++1).

Preparation 45

4-Bromo-1-(2-fluorophenyl)-3-phenyl-1H-pyrazole 1-(2-Fluorophenyl)-3-phenyl-1-H-pyrazole Add dioxane (7 mL) to a mixture of 3-phenyl-1H-pyrazole (2 g, 13.9 mmol), copper iodide (132 mg, 0.05 mmol) and potassium carbonate (555 mg, 4.2 mmol). Add 2-fluoroiodobenzene (1.94 mL, 16.6 mmol), trans-cyclohexyldiamine (0.35 mL, 2.78 mmol). Heat at 110° C. for about 18 hours. Cool to RT and filter through a silica gel pad eluting with ethyl acetate. Concentrate and purify (silica gel chromatography, eluting with hexane:ethyl acetate 84:16) to give the desired compound (36%).
MS (ES): m/z=239.1 ($M^+$+1).

Bromination
Beginning with 1-(2-fluorophenyl)-3-phenyl-1-H-pyrazole the title compound is prepared essentially as described in Preparation 27.
MS (ES): m/z=317.0 ($M^+$+1).

Preparation 46

2,6-Difluoro-4-pyrrolidin-1-yl ethoxy)benzaldehyde 1-(3,5-Difluorophenoxymethyl)pyrrolidine Add pyrrolidin-1-yl-ethanol hydrochloride (1.5 g) to a mixture of 3,5-difluorophenol (1.0 g, 7.68 mmol), cesium carbonate (8.78 g, 26.9 mmol), sodium iodide (1.15 g, 7.67 mmol) in DMF (20 mL). Stir at RT overnight. Concentrate and purify (silica gel chromatography eluting with ethyl acetate:hexane 1:1) to give the desired compound as an oil (0.8 g, 50%).

Formylation
Cool a mixture of 1-(3,5-difluorophenoxymethyl)pyrrolidine (0.1 g, 0.46 mmol) and THF (5 mL) to −78° C. under a nitrogen atmosphere. Add butyllithium (0.29 mL, 1.6 M in THF, 0.46 mmol)) and N,N,N',N'-tetramethylethylenediamine (0.5 mL, 3.3 mmol) and stir for 30 min. Add DMF (0.07 mL) and stir at RT for 60 min. Quench by pouring the reaction mixture into a mixture of cold saturated aqueous ammonium chloride and ethyl acetate. Separate the layers, wash the organic phase with water and concentrate to give the desired compound as an oil (0.10 g, 94%).

Preparation 47

2,6-Bis(trifluoromethyl)benzaldehyde 2,6-Bis(trifluoromethyl)benzyl alcohol

A mixture of 80 mL of THF and t-BuOK (7.0 g, 62.5 mmol) is added to a 250 mL four-neck flask equipped with a mechanical stirrer, a thermometer, a gas inlet tube and a 100 mL dropping funnel with a gas outlet tube. Cool down to −70° C. and 2,6-bis(trifluoromethyl)benzene (8.0 mL, 10.7 g, 50.0 mmol) is added dropwise and keep agitating ~−70° C. for 30 min. Add n-BuLi (0.10 mol, 2.87 M in hexanes 35.0 mL, 100.0 mmol) dropwise over 30 min with agitation at ~−70° C. for 60 min. Paraformaldehyde (6.0 g, 0.20 mol) is added and keep agitating ~70° C. for 30 min, then gradually warm to room temperature for 3 h. Pour mixture into conc HCl (10 mL) and ice water (300 mL), and stir for 1 h. Extract with hexanes (3×50 mL). Wash the combined organic layers with 50 mL of brine, dry over anhydrous $Na_2SO_4$, filter and concentrate. The crude product is vacuum distilled (72-76° C. at 4-5 mm Hg) to give the desired compound (5 g).
MS m/z=244 ($M^+$).

Oxidation
A solution of 2,6-bis(trifluoromethyl)benzylalcohol (6.0 g, 24.6 mmol) in methylene chloride (10 mL) is added to a mixture of pyridinium chlorochromate (10.0 g, 46.3 mmol) in methylene chloride (60 mL). Stirred at RT overnight Add hexane (150 mL) with rigorous stirring. Filtered through a pad of celite and concentrate to give the desired compound as a clear oil (5.20 g, 87%).
MS m/z=242 ($M^+$).

Preparation 48

1-(2-Amino-3-isobutyl-3H-benzimidazol-5-yl)-2-phenylethane-1,2-dione

1-Isobutyl-6-phenylethynyl-1H-benzimidazol-2-ylamine

Heat a mixture of $Pd(OAc)_2$ (1.25 g, 5.59 mmol), CuI (0.42 g, 2.23 mmol), $P(t-Bu)_3$ (2.76 mL, 11.2 mmol), $K_2CO_3$ (30.3 g, 223.8 mmol) and 6-bromo-1-isobutyl-1H-benzimidazol-2-ylamine (30 g, 111.9 mmol) in DMSO (200 mL) at 70° C. Add phenylacetylene (14.6 mL, 133.4 mmol) and heat the mixture for 6 hours at 70° C. Cool and dilute with $H_2O$. Filter the residue through a pad of celite. Recrystallize the crude mixture in toluene to give the desired compound as a white solid (19.68 g, 60%).
MS (ES): m/z=290.0

Oxidation
Add a solution of 1-isobutyl-6-phenylethynyl-1H-benzimidazol-2-ylamine (9.8 g, 33.8 mmol) in acetone (200 mL) into a solution mechanically stirred of $NaHCO_3$ (1.7 g, 26.3 mmol) and $MgSO_4$ (8.1 g, 67.6 mmol) in water (250 mL). Add $KMnO_4$ (21.3 g, 135 mmol) and stir for 3 h while cooling to RT. Add acetone (25 mL) and stir for 1.5 h. Add $Na_2SO_3$ (9.6 g, 76.05 mmol), and stir overnight. Filter the mixture through a pad of celite washing with a 1:1 mixture acetone:water (400 mL). Evaporate the resultant filtrate in vacuo, and purified (silica gel chromatography eluting with dichloromethane:methanol from 100:0 to 98:2) to give the title compound (3.5 g, 33% yield).
MS (ES): m/z=322

Preparation 49

1-[2-Amino-3-(1-(S)-methyl-2,2-dimethylpropyl)-3H-benzimidazol-5-yl]-2-phenylethane-1,2-dione Dissolve 6-phenylethynyl-1-(1-(L)-methyl-2,2-dimethylpropyl)-1H-benzimidazol-2-ylamine (2.476 g, 0.0078 mol) in acetone and cool in an ice bath. Dissolve $KMnO_4$ (2.5 g) in 1 M pH7 phosphate buffer (65 mL) and add to reaction vessel. Stir 40 minutes in an ice bath then warm to ambient temperature and stir 18 hours. Add saturated $Na_2SO_3$ (100 mL) and stir 30 minutes. Dilute with dichloromethane add celite and filter. Separate layers and evaporate organic layer. Purify on silica gel with dichloromethane/methanol mixtures to give 1.93 g (70%) of the desired compound as a foam.
MS (ES): m/z=350.3 ($M^+$+H).

Preparation 50

1-[2-Amino-3-(1-(R)-methyl-2,2-dimethylpropyl)-3H-benzimidazol-5-yl]-2-phenylethane-1,2-dione Beginning with 6-phenylethynyl-1-(1-(R)-methyl-2,2-dimethylpropyl)-1H-benzimidazol-2-ylamine (1.00 g), the desired compound is prepared (0.57 g) essentially as described in Preparation 49.

MS (ES): m/z=350.3 (M$^+$+H).

Preparation 51

1-isopropylsulfonyl-2-amino-benzimidazole-6-boronic acid

Charge a 5 L round bottom flask equipped with dry ice/acetone bath, nitrogen atmosphere, mechanical stirrer, thermocouple, and addition funnel with septum with 1-isopropylsulfonyl-2-amino-6-iodobenzimidazole (125 g, 342 mmol) and tetrahydrofuran (1.2 L) and cool to −77° C. (results in a slurry). To this slurry add phenyllithium (1.8 M in cyclohexane/diethyl ether, 599 mL, 1078 mmol) over 25 minutes keeping the temperature below −67° C. After stirring the resulting green slurry for 20 minutes while cooling to −77° C., add tert-butyllithium (1.7 M in pentane, 503 mL, 856 mmol) over 25 minutes keeping the temperature of the reaction below −67° C. Stir the mixture at −75° C. for 40 minutes then add triisopropyl borate (276 mL, 1198 mmol) over 15 minutes keeping the temperature below −65° C. Warm the resulting slurry slowly to 0° C. over 2 hours, then add a mixture of concentrated hydrochloric acid and water (400 mL) until pH 2 is reached. Stir the mixture for 1 hour then adjust to pH>12 with 5 N sodium hydroxide while keeping the temperature <10° C. Add water (1 L), and separate the layers. Wash the aqueous layer with ethyl acetate (300 mL) then adjust to pH 6 with concentrated hydrochloric acid. Extract the mixture with ethyl acetate (2×700 mL), dry the combined extracts over sodium sulfate, filter, and concentrate in vacuo to an orange paste (116 g). Dissolve the paste in warm (~60° C.) 2-propanol (360 mL) then add water (1.4 L). Cool the solution to 0° C. for 3 hours. Collect the resulting solid by filtration, wash with water then air-dry to constant weight to afford the title compound (34.9 g, 36% yield) as light tan crystals. Obtain a second crop from the filtrate (4.95 g, 41% yield overall). MS (ES$^+$): m/z=284 (M+H)$^+$

Preparation 52

1-dimethylaminosulfonyl-2-amino-6-iodobenzimidazole

1 dimethylaminosulfonyl-2-amino-benzimidazole

To a solution of sodium hydroxide (1.8 g) in water (9 mL) add acetonitrile (44 mL). To this solution, add 2-aminobenzimidazole (3.0 g, 22.5 mmol) and dimethylsulfamoyl chloride (2.4 mL, 22.5 mmol). Stir the reaction mixture at room temperature, overnight. Then, cool the mixture at 0° C. and the product crystallized from solution. Filter the product and dry it in vacuum to provide 5.0 g (90% yield) of the title compound as a white solid. MS (ES$^+$): m/z=241.1 (M+H)$^+$ Halogenation Add 1-dimethylaminosulfonyl-2-amino-benzimidazole (1.0 g, 4.2 mmol) to acetic acid (10 mL) to form a solution. To this solution, add N-iodosuccinimide (0.945 g, 4.2 mmol) and heat the reaction mixture at 55° C. overnight. Cool the mixture at 0° C. and add water. The product crystallized from solution. Filter the solid and dry it in vacuum to provide 1.5 g (99%) of title compound. MS (ES$^+$): m/z=366.9 (M+H)$^+$

Preparation 53

4-bromo-5-methyl-3-phenylisoxazole

Beginning with acetophenone oxime, the title compound is prepared essentially as described by Kumar (*Adv. Synth. Catal.*, 344(10), 1146-1151 (2002)).

MS (ES): m/z=238.0, 240.0 (M$^+$+H)

Preparation 54

2-(tert-butyl)-4-(4-fluorophenyl)-5-bromooxazole

2-(tert-butyl)-4-(4-fluorophenyl)oxazole

Stir a mixture of 2-bromo-4'-fluoroacetophenone (100 g, 460 mmol) and 2,2-dimethylpropionamide (93.06 g, 20 mmol) in 1,4-dioxane (600 mL) at reflux for 2 days. Filter the reaction mixture and concentrate the filtrate under reduced pressure. Subject the residue to silica gel chromatography, eluting with 60:1 hexane:ethyl acetate to provide 55 g (55%) of the desired compound.

MS (ES): m/z=220.1

Bromination

Add a solution of bromine (774 µL, 7.2 mmol) in chloroform (15 mL) to a solution of 2-(tert-butyl)-4-(4-fluorophenyl)oxazole (2.20 g, 10.04 mmol) in chloroform (60 mL). Stir at room temperature for 3 hours. Add saturated aqueous sodium thiosulfate. Extract with dichloromethane. Wash combined organic phases with saturated aqueous sodium chloride and dry over sodium sulfate. Concentrate under reduced pressure and subject the residue to silica gel chromatography, eluting with 60:1 hexane:ethyl acetate to provide 2.25 g (75%) of the title compound.

MS (ES): m/z=298.0

Preparation 55

2-tert-butyl)-4-(2,4-difluorophenyl)-5-bromooxazole

Beginning with 2-bromo-2',4'-difluoroacetophenone, the title compound may be prepared essentially as described in Preparation 54.

MS (ES): m/z=316.

EXAMPLE 1

1-Cyclopentyl-2-amino-6-(2-(2,6-difluorophenyl)-4-phenyl-1H-imidazol-5-yl)-1H-benzimidazole Heat a mixture of 1-(2-amino-1-cyclopentyl-1H-benzimidazol-6-yl)-2-(tert-butyldimethylsilyl)oxy-2-(phenyl)acetamide (0.39 g, 0.88 mmol), 2,6-difluorobenzaldehyde (0.1 mL, 0.97 mmol), copper(II) acetate (0.32 g, 1.76 mmol) and ammonium acetate (0.67 g, 8.8 mmol) in 15 ml acetic acid at 105° C. for 4 hours. Cool the solution and then pour into 3:1 aqueous ammonium chloride:ammonium hydroxide. Add 20 mL of 4:1 ethyl acetate:methanol. Separate the organic layer and wash sequentially with saturated aqueous sodium chloride and water. Dry over magnesium sulfate and concentrate under reduced pressure. Subject the residue to silica gel chromatography, eluting with dichloromethane containing 10% methanol to provide the title compound (22%).

MS (ES$^+$): 456.3

The compounds of EXAMPLES 2-3 are prepared essentially as described in EXAMPLE 1.

| EXAMPLE | Compound | MS (ESI$^+$): m/z |
|---|---|---|
| 2 | 1-Phenyl-2-amino-6-(2-(2,6-difluorophenyl)-4-phenyl-1H-imidazol-5-yl)-1H-benzimidazole | 464.2 |
| 3 | 1-(Pent-3-yl)-2-amino-6-(2-(2,6-difluorophenyl)-4-phenyl-1H-imidazol-5-yl)-1H-benzimidazole | 458.3 |

EXAMPLE 4

1-isopropyl-2-amino-6-(2,4-diphenyl-1H-imidazol-5-yl)-1H-benzimidazole

Stir a mixture of 2,4-diphenyl-5-(3-(isopropyl)amino-4-aminophenyl)imidazole (0.075 g, 0.20 mmol), lithium methoxide (0.41 mmol, 15 mg) and cyanogen bromide (0.6 mmol, 0.2 ml of 3N in dichloromethane) in dichloromethane (5 ml) under nitrogen for 1 hour. Add ethanol (5 ml), and continue stirring for 5 hours. Pour reaction mixture over an SCX column, and elute sequentially with methanol followed by 2N ammonia in methanol. Combine the basic fractions and concentrate under reduced pressure. Subject the residue to silica gel chromatography, eluting with 9:1 dichloromethane: methanol to provide the title compound as a white solid (30 mg, 38%).

MS (ES): m/z=394.3.

The compounds of EXAMPLES 5-43 may be prepared essentially as described in EXAMPLE 4. Where compounds are named as salts, the salts were prepared essentially as described in the General Method for Salt Formation.

| EXAMPLE | Compound | MS (ESI$^+$): m/z = |
|---|---|---|
| 5 | 1-(Cyclopropylmethyl)-2-amino-6-(2-(2,6-difluorophenyl)-4-phenyl-1H-imidazol-5-yl)-1H-benzimidazole | 442.2 |
| 6 | 1-(Isobutyl)-2-amino-6-(2-(2,6-difluorophenyl)-4-phenyl-1H-imidazol-5-yl)-1H-benzimidazole | 444.2 |
| 7 | 1-(Isopropyl)-2-amino-6-(2-(2,6-difluorophenyl)-4-phenyl-1H-imidazol-5-yl)-1H-benzimidazole | 430.2 |
| 8 | 1-(Propyl)-2-amino-6-(2-(2,6-difluorophenyl)-4-phenyl-1H-imidazol-5-yl)-1H-benzimidazole | 430.2 |
| 9 | 1-(Methyl)-2-amino-6-(2-(2,6-difluorophenyl)-4-phenyl-1H-imidazol-5-yl)-1H-benzimidazole | 402.2 |
| 10 | 1-(Ethyl)-2-amino-6-(2-(2,6-difluorophenyl)-4-phenyl-1H-imidazol-5-yl)-1H-benzimidazole | 416.2 |
| 11 | 1-(Butyl)-2-amino-6-(2-(2,6-difluorophenyl)-4-phenyl-1H-imidazol-5-yl)-1H-benzimidazole | 444.2 |
| 12 | 1-(2,2-Dimethylpropyl)-2-amino-6-(2-(2,6-difluorophenyl)-4-phenyl-1H-imidazol-5-yl)-1H-benzimidazole | 485.3 |
| 13 | 1-(Benzyl)-2-amino-6-(2-(2,6-difluorophenyl)-4-phenyl-1H-imidazol-5-yl)-1H-benzimidazole | 478.2 |
| 14 | 1-(Cyclohexylmethyl)-2-amino-6-(2-(2,6-difluorophenyl)-4-phenyl-1H-imidazol-5-yl)-1H-benzimidazole | 484.3 |
| 15 | 1-(Isobutyl)-2-amino-6-(2-(tert-butyl)-4-phenyl-1H-imidazol-5-yl)-1H-benzimidazole | 388.3 |
| 16 | 1-(Isobutyl)-2-amino-6-(2-(isopropyl)-4-phenyl-1H-imidazol-5-yl)-1H-benzimidazole | 374.2 |
| 17 | 1-(Isobutyl)-2-amino-6-(2-(trifluoromethyl)-4-phenyl-1H-imidazol-5-yl)-1H-benzimidazole | 400.2 |
| 18 | 1-(Isobutyl)-2-amino-6-(2-(methyl)-4-phenyl-1H-imidazol-5-yl)-1H-benzimidazole | 346.2 |
| 19 | 1-(Isobutyl)-2-amino-6-(2-(2-chloro-6-fluorophenyl)-4-phenyl-1H-imidazol-5-yl)-1H-benzimidazole | 460.9 |
| 20 | 6-[2-(2,6-Dichlorophenyl)-5-phenyl-1H-imidazol-4-yl]-1-isobutyl-1H-benzimidazol-2-ylamine methanesulfonate | 476.2 [M + H] |
| 21 | 6-[2-(2-Chloro-6-fluorophenyl)-5-(4-fluorophenyl)-1H-imidazol-4-yl]-1-isobutyl-1H-benzimidazol-2-ylamine methanesulfonate | 478.2 [M + H] |
| 22 | 6-[2-(2,6-Dichlorophenyl)-5-(4-fluorophenyl)-1H-imidazol-4-yl]-1-isobutyl-1H-benzimidazol-2-ylamine methanesulfonate | 494.2 [M + H] |
| 23 | 6-[2-(2,6-Dichlorophenyl)-5-phenyl-1H-imidazol-4-yl]-1-(2,2-dimethylpropyl)-1H-benzimidazol-2-ylamine methanesulfonate | 490.2 [M + H] |
| 24 | 1-Cyclopropylmethyl-6-[2-(2,6-dichlorophenyl)-5-(2,4-difluorophenyl)-1H-imidazol-4-yl]-1H-benzimidazol-2-ylamine methanesulfonate | 510.3 [M + H] |

-continued

| EXAMPLE | Compound | MS (ESI+): m/z = |
|---|---|---|
| 25 | 6-[2-(2-Chloro-6-fluorophenyl)-5-(2,4-difluorophenyl)-1H-imidazol-4-yl]-1-cyclopropylmethyl-1H-benzimidazol-2-ylamine methanesulfonate | 494.3 [M + H] |
| 26 | 1-Cyclopropylmethyl-6-[2-(2,4-difluorophenyl)-5-(2-fluoro-6-trifluoromethylphenyl)-1H-imidazol-4-yl]-1H-benzimidazol-2-ylamine methanesulfonate | 494.3 [M + H] |
| 27 | 1-Cyclopropymethyl-6-[5-(2,4-difluorophenyl)-2-(2,6 difluorophenyl)-1H-imidazol-4-yl]-1H-benzimidazol-2-ylamine methanesulfonate | 528.2 [M + H] |
| 28 | 6-[2-Cyclopropyl-5-(2,4-difluorophenyl)-1H-imidazol-4-yl]-1-cyclopropylmethyl-1H-benzimidazol-2-ylamine | 406.3 [M + H] |
| 29 | 6-[2-tert-Butyl-5-(2,4-difluorophenyl)-1H-imidazol-4-yl]-1-cyclopropylmethyl-1H-benzimidazol-2-ylamine methanesulfonate | 422.2 [M + H] |
| 30 | 1-Isobutyl-6-[2-(3-methylthiophen-2-yl)-5-phenyl-1H-imidazol-4-yl]-1H-benzimidazol-2-ylamine methanesulfonate | 428.3 [M + H] |
| 31 | 6-[2-(2,6-Dichlorophenyl)-5-(2,4-difluorophenyl)-1H-imidazol]-1-(2,2-dimethylpropyl)-1H-benzimidazol-2-ylamine methansulfonate | 526.3 [M + H] |
| 32 | 6-[2-(2-Chloro-6-fluorophenyl)-5-(2,4-difluorophenyl)-3H-imidazol-4-yl]-1-isobutyl-1H-benzimidazol-2-ylamine | 495.93 |
| 33 | 6-[2-(2,6-Dichlorophenyl)-5-(2,4-difluorophenyl)-3H-imidazol-4-yl]-1-isobutyl-1H-benzimidazol-2-ylamine | 512.38 |
| 34 | 6-[2-tert-Butyl-5-(2,4-difluorophenyl)-3H-imidazol-4-yl]-1-isobutyl-1H-benzimidazol-2-ylamine di-methanesulfonate | 423.50 |
| 35 | 6-[2-Cyclopropyl-5-(2,4-difluorophenyl)-3H-imidazol-4-yl]-1-isobutyl-1H-benzimidazol-2-ylamine di-methanesulfonate | 407.46 |
| 36 | 6-[2-(2,6-Difluoro-4-(pyrrolidin-1-ylethoxy)-phenyl)-5-phenyl-3H-imidazol-4-yl]-1-isobutyl-1H-benzimidazol-2-ylamine methanesulfonate | 556.66 |
| 37 | 6-[2-(2-Fluoro-6-trifluoromethylphenyl)-5-phenyl-3H-imidazol-4-yl]-1-isobutyl-1H-benzimidazol-2-ylamine methanesulfonate | 493.51 |
| 38 | 6-[2-(2-Chloro-6-fluorophenyl)-5-(2,4-difluorophenyl)-3H-imidazol-4-yl]-1-isobutyl-1H-benzimidazol-2-ylamine | 495.93 |
| 39 | 6-[2-(2,6-Difluorophenyl)-5-phenyl-3H-imidazol-4-yl]-1-(3-fluorobenzyl)-1H-benzimidazol-2-ylamine methanesulfonate | 496.3 |
| 40 | 6-[2-(4-Chlorophenyl)-5-(4-fluorophenyl)-3H-imidazol-4-yl]-1-isobutyl-1H-benzimidazol-2-ylamine | 460.1 |
| 41 | 6-[5-(4-Fluorophenyl)-2-(2-trifluoromethylphenyl)-3H-imidazol-4-yl]-1-isobutyl-1H-benzimidazol-2-ylamine | 494.1 |
| 42 | 6-[2-tert-Butyl-5-(4-fluorophenyl)-3H-imidazol-4-yl]-1-isobutyl-1H-benzimidazol-2-ylamine | 406.3 |
| 43 | 6-[2-Cyclopropyl-5-(4-fluorophenyl)-3H-imidazol-4-yl]-1-isobutyl-1H-benzimidazol-2-ylamine | 390.3 |

EXAMPLE 44

1-Cyclopropylmethyl-6-(2-(2,6-difluorophenyl)-4-phenyl-1H-imidazol-5-yl)-1H-benzimidazole Heat a mixture of 2-(2,6-difluorophenyl)-4-phenyl-5-(3-(cyclopropylmethyl)amino-4-aminophenyl)imidazole (0.100 g, 0.24 mmol) and trimethylorthoformate (2 mL) in acetic acid (4 mL) at 120° C. for 1 hour. Cool the reaction mixture to room temperature and concentrate under reduced pressure. Dilute the residue with methanol and pour over an SCX column, eluting sequentially with methanol followed by 2N ammonia in methanol. Combine the basic fractions and concentrate under reduced pressure. Subject the residue to silica gel chromatography, eluting with 95:5 dichloromethane:methanol to provide the title compound as a white solid.

MS (ES): m/z=427.2.

The compounds of EXAMPLES 45-47 may be prepared essentially as described in EXAMPLE 44.

| EXAMPLE | Compound | MS (ESI+): m/z = |
|---|---|---|
| 45 | 1-(Isobutyl)-6-(2-(2,6-difluorophenyl)-4-phenyl-1H-imidazol-5-yl)-1H-benzimidazole | 429.2 |
| 46 | 1-(Isopropyl)-6-(2-(2,6-difluorophenyl)-4-phenyl-1H-imidazol-5-yl)-1H-benzimidazole | 415.2 |
| 47 | 1-(cyclopropylmethyl)-6-(2-(4-chlorophenyl)-4-phenyl)-1H-imidazol-5-yl)-1H-benzimidazole dimethanesulfonate | 425.2 |

General Method for Salt Formation

Add one or two equivalents of an acid to a solution of one equivalent of the free base of a compound of Formula I in methanol. Add ethyl acetate until the solution is cloudy. Allow the cloudy solution to stand until crystallization is complete, typically for one hour to two days. Filter the suspension, wash the solid, and dry under reduced pressure to provide the desired salt. Alternatively, concentrate the methanol salt solution under reduced pressure. Add dichloromethane to the residue and concentrate again under reduced pressure to provide the desired salt.

The compounds of EXAMPLES 48-54 may be prepared essentially as described in the General Method for Salt Formation.

| EXAMPLE | Compound | MS (ESI+): m/z = |
|---|---|---|
| 48 | 1-(Cyclopropylmethyl)-6-(4-(2-(piperidin-1-yl)eth-1-oxyphenyl)-4-phenyl-1H-imidazol-5-yl)-1H-benzimidazole hydrochloride | 518.2 |
| 49 | 1-(2,2-Dimethylpropyl)-6-(2-(2,6-difluorophenyl)-4-phenyl-1H-imidazol-5-yl)-1H-benzimidazole di-methanesulfonate | 443.3 |
| 50 | 1-(Butyl)-6-(2-(2,6-difluorophenyl)-4-phenyl-1H-imidazol-5-yl)-1H-benzimidazole di-methanesulfonate | 429.2 |
| 51 | 1-(Ethyl)-6-(2-(2,6-difluorophenyl)-4-phenyl-1H-imidazol-5-yl)-1H-benzimidazole di-methanesulfonate | 401.2 |
| 52 | 1-(Methyl)-6-(2-(2,6-difluorophenyl)-4-phenyl-1H-imidazol-5-yl)-1H-benzimidazole di-methanesulfonate | 387.2 |
| 53 | 1-(Propyl)-6-(2-(2,6-difluorophenyl)-4-phenyl-1H-imidazol-5-yl)-1H-benzimidazole di-methanesulfonate | 415.2 |
| 54 | 6-(2-(2,6-Difluorophenyl)-4-phenyl-1H-imidazole-5-yl)-1H-benzimidazole di-methanesulfonate | 373.1 |

EXAMPLE 55

1-Isobutyl-2-amino-6-(1-cyclohexyl-4-phenyl-1H-imidazol-5-yl)-1H-benzimidazole

Add cyanogen bromide (101 mg, 0.96 mmol) to a solution of 1-(cyclohexyl)-4-phenyl-5-(3-(isobutylamino)-4-aminophenyl)-1H-imidazole (250 mg, 0.64 mmol) in 6 mL ethanol. Stir over night at room temperature. Add saturated aqueous sodium carbonate and extract well with 9:1 ethyl acetate:methanol. Combine the organic phases, dry over magnesium sulfate, and concentrate under reduced pressure. Subject the residue to silica gel chromatography, eluting with a gradient of 5-8% methanol in dichloromethane to provide the title compound (52%).

MS (ES): m/z=414.2 (M++1).

EXAMPLE 56

Isobutyl-6-(1-cyclohexyl-4-phenyl-1H-imidazol-5-yl)-1H-benzimidazole

Heat a mixture of 1-(cyclohexyl)-4-phenyl-5-(3-(isobutylamino)-4-aminophenyl)-1H-imidazole (83 mg, 0.21 mmol) and 3 mL trimethyl orthoformate at 120° C. for 6 hours. Cool to room temperature and concentrate under reduced pressure. Subject the residue to silica gel chromatography, eluting with 3:1 ethyl acetate:hexanes to provide the title compound (73%).

MS (ES): m/z=399.2 (M++1).

EXAMPLE 57

1-Isobutyl-2-methyl-6-(1-cyclohexyl-4-phenyl-1H-imidazol-5-yl)-1H-benzimidazole

Heat a mixture of 1-(cyclohexyl)-4-phenyl-5-(3-(isobutylamino)-4-aminophenyl)-1H-imidazole (103 mg, 0.26 mmol) and 3 mL triethylorthoformate at 120° C. for 3 hours. Cool to room temperature and concentrate under reduced pressure. Subject the residue to silica gel chromatography, eluting with 2:1 ethyl acetate:hexanes to provide the title compound (45%).

MS (ES): m/z=413.2

The compound of EXAMPLE 58 may be prepared essentially as described in EXAMPLE 57.

| EXAMPLE | Compound | MS (ESI+): m/z = |
|---|---|---|
| 58 | 6-[2-(2,6-difluorophenyl)-5-phenyl-1H-imidazol-4-yl]-1-isobutyl-2-methyl-1H-benzimidazole methanesulfonate | 443.2 |

EXAMPLE 59

1-Isobutyl-2-amino-6-(2-(4-fluorophenyl)-6,7-dihydro-5H-pyrrolo[1,2-a]imidazol-3-yl)-1H-benzimidazole di-methanesulfonic acid Bubble nitrogen through a solution of 3-bromo-2-(4-fluorophenyl)-6,7-dihydro-5H-pyrrolo[1,2-a]imidazole (750 mg, 2.67 mmol) in dimethoxyethane (20 ml). Add bis(triphenylphosphine)palladium(II) chloride (175 mg, 0.095 mmol) and stir at room temperature for 3 minutes. Add (1-isobutyl-2-amino-1H-benzimidazol-6-yl)boronic acid (750 mg, 3.211 mmol) by 2M aqueous sodium carbonate (2.7 mL, 5.40 mmol). Heat at 90° C. for 16 hours. Cool to room temperature, dilute with water (50 ml), and extract with ethyl acetate (150 ml). Dry over magnesium sulfate and concentrate under reduced pressure. Subject the residue to HPLC (Xterra MS C18 5 µm, 19×100 mm; Solvent A: 10 mM ammonium carbonate at pH 9; Solvent B: acetonitrile; Gradient: from 35 to 50% B in 8 minutes and then 50 95% B in 1 minute; Flow rate: 20 mL/min) to provide 1-isobutyl-2-amino-6-(2-(4-fluorophenyl)-6,7-dihydro-5H-pyrrolo[1,2-a]imidazol-3-yl)-1H-benzimidazole (325 mg, 31%). MS (ES): m/z=390 (M++H) The free base is treated with two equivalents of methanesulfonic acid essentially as previously described to provide the title compound (50%).

EXAMPLE 60

1-Isobutyl-2-amino-6-(2-phenyl-1H-imidazol-1-yl)-1H-benzimidazole

Add cyanogen bromide (177 mg, 1.67 mmol) to a solution of 1-(3-(isobutylamino)-4-aminophenyl)-2-phenyl-1H-imidazole (410 mg, 1.34 mmol) in 10 mL isopropanol cooled to 0° C. Stir for one hour at this temperature and then stir at room temperature over night. Dilute with ethyl acetate and wash with 1N sodium hydroxide. Dry the organic layer over sodium sulfate, filter, and concentrate under reduced pressure. Subject the residue to radial silica gel chromatography, eluting with methanol containing 4% methanol to provide the title compound as a tan solid (220 mg, 50%).

MS (ES): m/z=332.0 (M$^+$+1)

EXAMPLE 61

1-Isobutyl-2-amino-6-(3-phenyl-1H-pyrazol-4-yl)-1H-benzimidazole

Beginning with 3-phenyl-4-(3-(isobutylamino)-4-aminophenyl)-1H-pyrazole (104 mg, 0.34 mmol), the title compound is prepared essentially as described in EXAMPLE 4.

MS (ES): m/z=332.2 (M$^+$+1)

EXAMPLE 62

1-Isopropyl-2-amino-6-(4-phenyl-2H-[1,2,3]triazol-5-yl)-1H-benzimidazole

Beginning with 4-phenyl-5-(3-(isopropylamino)-4-aminophenyl)-[1,2,3]triazole (0.150 g), the title compound is prepared essentially as described in EXAMPLE 4 (0.050 g, 30%).

MS (ES): m/z=319.38 (M$^+$+H).

EXAMPLE 63

1-Isobutyl-2-amino-6-(4-phenyl-2H-[1,2,3]triazol-5-yl)-1H-benzimidazole

Beginning with 4-phenyl-5-(3-(isobutylamino)-4-aminophenyl)-[1,2,3]triazole, the title compound is prepared essentially as described in EXAMPLE 4.

MS (ES): m/z=333.41 (M$^+$+H).

EXAMPLE 64

1-Isopropyl-6-(4-phenyl-2H-[1,2,3]triazol-5-yl)-1H-benzimidazole

Beginning with 4-phenyl-5-(3-(isopropylamino)-4-aminophenyl)-[1,2,3]triazole (0.150 g), the title compound is prepared essentially as described in EXAMPLE 45 (0.050 g, 32%).

MS (ES): m/z=304.37 (M$^+$+H).

EXAMPLE 65

1-Isobutyl-6-(4-phenyl-2H-[1,2,3]triazol-5-yl)-1H-benzimidazole

Beginning with 4-phenyl-5-(3-(isobutylamino)-4-aminophenyl)-[1,2,3]triazole, the title compound is prepared essentially as described in EXAMPLE 45.

MS (ES): m/z=318.40 (M$^+$+H).

EXAMPLE 66

1-Isobutyl-2-amino-5-(2-(2-chloro-6-fluorophenyl)-4-phenyl-1H-imidazol-5-yl)-1H-benzimidazole Beginning with 2-(2-chloro-6-fluorophenyl)-4-phenyl-5-(3-amino-4-(isobutyl-amino)phenyl)-1H-imidazole (0.26 g), the title compound is prepared (0.149 g, 55%) essentially as described in EXAMPLE 4.

MS (ES): m/z=460.95 (M$^+$+H).

EXAMPLE 67

1-(3-Methylbut-2-yl)-2-amino-6-(2-methyl-4-(2,4-difluorophenyl)-1H-imidazol-5-yl)-1H-benzimidazole methanesulfonate Combine 1-benzyl-2-methyl-4-(3-(N-[3-methylbut-2-yl]-N-[cyano]amino)-4-nitrophenyl)-5-(2,4-difluorophenyl)-1H-imidazole-(0.122 g, 0.24 mmol), 10% palladium on carbon (90 mg), and 1,4-cyclohexadiene (2 mL) in absolute ethanol (10 mL) and heat to 95° C. in a sealed vessel for 18 hours. Cool to room temperature, filter through celite, and concentrate the filtrate under reduced pressure. Subject the residue to silica gel chromatography, eluting with dichloromethane/methano/ammonia mixtures to give 0.077 g (0.195 mmol) of 1-(3-methylbut-2-yl)-2-amino-6-(2-methyl-4-(2,4-difluorophenyl)-1H-imidazol-5-yl)-1H-benzimidazole. Dissolve in 10% methanol/dichloromethane, add 1.0 equivalent methanesulfonic acid, remove solvent under a stream of nitrogen and finally under high vacuum to give 0.094 g of the title compound.

MS (ES+H): m/z=396.2.

The compounds of EXAMPLES 68-69 may be prepared essentially as described in EXAMPLE 67.

| EXAMPLE | Compound | MS (ESI$^+$): m/z = |
|---|---|---|
| 68 | (+/−)-6-[2-(2,6-Difluorophenyl)-5-phenyl-3H-imidazol-4-yl]-1-(1,2-dimethylpropyl)-1H-benzimidazol-2-ylamine methanesulfonate | 458.2 (M$^+$ + H) |
| 69 | (+/−)-6-[2-(2,6-Difluorophenyl)-5-phenyl-3H-imidazol-4-yl]-1-(1,2,2-trimethylpropyl)-1H-benzimidazol-2-ylamine methanesulfonate | 472.2 (M$^+$ + H) |

EXAMPLE 70

1-(Isobutyl)-6-(2-methyl-4-(2,4-difluorophenyl)-1H-imidazol-5-yl)-1H-benzimidazole methanesulfonate Heat a mixture of 1-benzyl-2-methyl-4-(3-(N-[isobutyl]]amino)-4-nitrophenyl)-5-(2,4-difluorophenyl)-1H-imidazole (0.055 g, 0.114 mmol), 20% palladium hydroxide on carbon wet (52 mg), and formic acid (0.3 mL) in methanol (5 mL) to 80° C. in a sealed vessel for 18 hours. Cool to room temperature, filter through Celite, and concentrate under reduced pressure. Subject to C18 reversed phase silica gel chromatography, eluting with water/acetonitrile/trifluoroacetic acid mixtures. Combine fractions containing product, add saturated sodium hydrogen carbonate, and remove organic solvents under reduced pressure. Extract product with 10% methanol/dichloromethane and dry with magnesium sulfate.

Concentrate under reduced pressure. Dissolve in 10% methanol/dichloromethane, add 1.0 equivalent methanesulfonic acid and remove solvents under a stream of nitrogen and finally under high vacuum to give 0.031 g (0.062 mmol) of the title compound.

MS (ES+H): m/z=367.2.

The compounds of EXAMPLE 71 may be prepared essentially as described in EXAMPLE 70.

| EXAMPLE | Compound | MS (ESI$^+$): m/z = |
|---|---|---|
| 71 | 1-(Isobutyl)-2-amino-6-(2-methyl-4-(2,4-difluorophenyl)-1H-imidazol-5-yl)-1H-benzimidazole | 382.2 (M$^+$ + H) |

EXAMPLE 72

1-(Isobutyl)-2-amino-6-(1-methyl-4-phenyl-1H-imidazol-5-yl)-1H-benzimidazole methanesulfonate 1-Isobutyl-2-amino-6-(methyliminomethyl)-1H-benzimidazole Add methylamine (3.0 mL, 6 mmol, 2M in tetrahydrofuran) to a solution 1-isobutyl-2-amino-6-formylbenzimidazole (475 mg, 2.19 mmol) in dimethylformamide (5 mL). Stir at room temperature for 18 hours. Concentrate under reduced pressure to provide the title compound (503 mg).

MS (ES): m/z=231.3 (M$^+$+1)

1-Isobutyl-2-amino-6-(1-methyl-4-phenyl-1H-imidazol-5-yl)-1H-benzimidazole

Heat a mixture of 1-isobutyl-2-amino-6-(methyliminomethyl)-1H-benzimidazole (504 mg, 2.19 mmol), α-(p-toluenesulfonyl)benzylisocyanide (1.48 g, 5.47 mmol), methanol (7 mL), and methylamine (5.5 mL, 2M in tetrahydrofuran) in a sealed tube at 80° C. for 20 hours. Cool to room temperature and concentrate under reduced pressure. Subject residue to silica gel chromatography, eluting with a 1:1 mixture of acetonitrile and dichloromethane containing 5% methanol to provide the desired compound.

MS (ES): m/z=346.2 (M$^+$+H).

Salt Formation

Treat a solution of 1 equivalent of 1-isobutyl-2-amino-6-(1-methyl-4-phenyl-1H-imidazol-5-yl)-1H-benzimidazole in dichloromethane with 1 equivalent of methanesulfonic acid. Stir for 10 minutes at room temperature. Concentrate under reduced pressure. Crystallize residue from warm ethyl acetate to provide the title compound.

EXAMPLE 73

1-(Isobutyl)-2-amino-6-(1-methyl-4-(4-fluorophenyl)-1H-imidazol-5-yl)-1H-benzimidazole methanesulfonate Beginning with 1-isobutyl-2-amino-6-(methyliminomethyl)-1H-benzimidazole (142 mg, 0.52 mmol), α-(p-toluenesulfonyl)-4-fluorobenzylisocyanide (302 mg, 1.05 mmol), methanol (2.5 ml), and methylamine (1.3 ml, 2M in tetrahydrofuran), 1-(isobutyl)-2-amino-6-(1-methyl-4 (4-fluorophenyl)-1H-imidazol-5-yl)-1H-benzimidazole may be prepared essentially as described in EXAMPLE 72. Treatment with 1 equivalent of methanesulfonic acid provides the title compound (114 mg).

MS (ES): m/z=364.3 (M$^+$+H).

EXAMPLE 74

1-Isobutyl-2-amino-6-(1-methyl-2-(4-chlorophenyl)-4-phenyl-1H-imidazol-5-yl)-1H-benzimidazole 1-Isobutyl-2-(N-[acetyl]amino)-6-(1-methyl-4-phenyl-1H-imidazol-5-yl)-1H-benzimidazole Stir a mixture of 1-isobutyl-2-amino-6-(1-methyl-4-phenyl-1H-imidazol-5-yl)-1H-benzimidazole (35 mg, 0.1 mmol), acetic anhydride (11.2 mg), triethylamine (11.1 mg), and dimethylaminopyridine (1.2 mg) in tetrahydrofuran (5 mL) for 24 hours at room temperature. Concentrate under reduced pressure and subject the residue to silica gel chromatography, eluting with 1:1 dichloromethane:acetonitrile to provide the desired compound (17 mg).

MS (ES): m/z=388.2 (M$^+$+H).

1-Isobutyl-2-(N-[acetyl]amino)-6-(1-methyl-2-bromo phenyl-1H-imidazol-5-yl)-1H-benzimidazole Add a solution of N-bromosuccinimide (7.1 mg) in acetonitrile (1.5 mL) dropwise over 5-10 minutes to a solution of 1-isobutyl-2-(N-[acetyl]amino)-6-(1-methyl-4-phenyl-1H-imidazol-5-yl)-1H-benzimidazole (16 mg, 0.04 mmol) in 2 mL acetonitrile at room temperature. Stir for 5 minutes after the addition is complete and then add pyridine (0.5 mL). Stir for 2-3 minutes, dilute with water, and extract well with ethyl acetate. Wash the combined ethyl acetate extracts with saturated aqueous sodium chloride, dry over sodium sulfate, filter, and concentrate under reduced pressure to provide the desired compound.

MS (ES): m/z=466.1 (M$^+$+H).

Coupling

Shake well a mixture of 1-isobutyl-2-(N-[acetyl]amino)-6-(1-methyl-3-bromo-4-phenyl-1H-imidazol-5-yl)-1H-benzimidazole (19 mg, 0.04 mmol), methanol (0.5 mL), and toluene (3 mL) in a sealed tube. Add 4-chlorophenylboronic acid (7.8 mg, 0.05 mmol), tetrakis(triphenylphosphine)palladium(0) (6 mg, 0.005 mmol), and 2M aqueous sodium carbonate (0.25 mL). Shake vigorously and heat at 85° C. for 6 hours. Cool the reaction mixture to room temperature, dilute with water, and extract well with ethyl acetate. Wash the combined ethyl acetate extracts and wash with saturated aqueous sodium chloride, dry over sodium sulfate, filter, and concentrate under reduced pressure. Subject the residue to silica gel chromatography, eluting with 1:1 dichloromethane: acetonitrile containing from 0-5% methanol to provide the title compound (6 mg).

MS (ES): m/z=456.2 (M$^+$+H).

The compounds of EXAMPLES 75 and 76 may be prepared as described in EXAMPLE 74.

| EXAMPLE | Compound | MS (ESI$^+$): m/z = |
|---|---|---|
| 75 | 1-Isobutyl-2-amino-6-(1-methyl-2-cyclohexyl-4-phenyl-1H-imidazol-5-yl)-1H-benzimidazole | 428.5 (M$^+$ + H) |
| z6 | 1-Isobutyl-2-amino-6-(1-methyl-2-cyclopropyl-4-phenyl-1H-imidazol-5-yl)-1H-benzimidazole | 386.7 (M$^+$ + H) |

EXAMPLE 77

6-[2-(2,6-Difluorophenyl)-5-phenyl-3H-imidazol-4-yl]-1-(1-(S)-methyl-2,2-dimethylpropyl)-1H-benzimidazol-2-ylamine methanesulfonate Add 1-[2-Amino-3-(1-(S)-methyl-2,2-dimethylpropyl)-3H-benzimidazol-5-yl]-2-phenyl-thane-1,2-dione (0.200 g, 0.57 mmol), 2,6-difluorobenzaldehyde (0.16 mL), ammonium acetate (0.25 g) and glacial acetic acid (1.5 mL) and heat to 120° C. for 18 hours. Cool to ambient temperature and evaporate under reduced pressure. Dissolve in dichloromethane and wash with water, saturated sodium bicarbonate, dry with magnesium sulfate, filter and purify on silica gel with 4% 2M ammonia-methanol/dichloromethane. Combine fractions and evaporate to dryness. Redissolve in 10% methanol/dichloromethane and add 1.0 equivalents methanesulfonic acid and evaporate to dryness to give 0.181 g (56%) of the title compound.

MS (ES): m/z=472.2 (M$^+$+1).

The compounds of EXAMPLES 78-89 may be prepared essentially as described in EXAMPLE 77.

EXAMPLE 90

3-(2,4-difluorophenyl)-4-(1-(isobutyl)-2-aminobenzimidazol-6-yl)pyrazole di-methanesulfonic acid Add trifluoroacetic acid containing 5% water (7 mL) to a solution of 1-trityl-3-(2,4-difluorophenyl)-4-(1-(isobutyl)-2-aminobenzimidazol-6-yl)pyrazole (417 mg, 0.68 mmol) in dichloromethane (3 mL) and methanol (6 mL). Heat at 75° C. for 1 hour. Cool to RT, concentrate and recrystallize from dichloromethane:methanol 90:10 (88%). Add to the free base 2 equivalents of methanesulfonic acid essentially as described in EXAMPLE 71.

MS (ES): m/z=368.2 (M$^+$+1).

EXAMPLE 91

1-(1-Fluorophenyl)-3-(phenyl)-4-(1-(isobutyl)-2-aminobenzimidazol-6-yl)pyrazole methanesulfonate Beginning with 4-bromo-1-(2-fluorophenyl)-3-phenyl-1H-pyrazole and (1-isobutyl-2-aminobenzimidazol-6-yl)boronic acid, the title compound is prepared essentially as

| EXAMPLE | Compound | MS (ESI$^+$): m/z = |
|---|---|---|
| 78 | 6-[2-(2,6-Difluorophenyl)-5-phenyl-3H-imidazol-4-yl]-1-(1-(R)-methyl-2,2-dimethylpropyl)-1H-benzimidazol-2-ylamine methanesulfonate | 472.2 (M$^+$ + H) |
| 79 | 6-[2-(2-Chloro-6-fluorophenyl)-5-phenyl-3H-imidazol-4-yl]-1-(1-(S)-methyl-2,2-dimethylpropyl)-1H-benzimidazol-2-ylamine methanesulfonate | 488.2 (M$^+$ + H) |
| 80 | 6-(2-tert-Butyl-5-phenyl-3H-imidazol-4-yl)-1-(1-(S)-methyl-2,2-dimethylpropyl)-1H-benzimidazol-2-ylamine methanesulfonate | 416.3 (M$^+$ + H) |
| 81 | 6-(2-tert-Butyl-5-phenyl-3H-imidazol-4-yl)-1-(1-(R)-methyl-2,2-dimethyl-propyl)-1H-benzimidazol-2-ylamine methanesulfonate | 416.3 (M$^+$ + H) |
| 82 | 6-[2-(2-Chloro-6-fluorophenyl)-5-phenyl-3H-imidazol-4-yl]-1-(1-(R)-methyl-2,2-dimethylpropyl)-1H-benzimidazol-2-ylamine methanesulfonate | 488.2 (M$^+$ + H) |
| 83 | 6-[2-(2,6-Dichlorophenyl)-5-phenyl-3H-imidazol-4-yl]-1-(1-(R)-methyl-2,2-dimethylpropyl)-1H-benzimidazol-2-ylamine methanesulfonate | 505.2 (M$^+$ + H) |
| 84 | 1-Neopentyl-2-amino-6-(2-(2-fluoro-6-trifluoromethylphenyl)-4-phenyl-1H-imidazol-5-yl)-1H-benzimidazole di-methanesulfonate | 508.1 (M$^+$ + H) |
| 85 | 6-[2-(4-Chlorophenyl)-5-phenyl-3H-imidazol-4-yl]-1-isobutyl-1H-benzimidazol-2-ylamine di-methanesulfonate | 442.1 |
| 86 | 1-Isobutyl-6-[5-phenyl-2-(2-trifluoromethylphenyl)-3H-imidazol-4-yl]-1H-benzimidazol-2-ylamine di-methanesulfonate | 476.4 |
| 87 | 6-(2-Cyclopropyl-5-phenyl-3H-imidazol-4-yl)-1-isobutyl-1H-benzimidazol-2-ylamine methanesulfonate | 372.2 |
| 88 | 1-Cyclopropylmethyl-6-[2-(2-fluoro-6-trifluoromethylphenyl)-5-phenyl-1H-imidazol-4-yl]-1H-benzimidazol-2-ylamine methanesulfonate | 491.2 |
| 89 | 6-[2-(2-Chloro-6-fluorophenyl)-5-phenyl-1H-imidazol-4-yl]-1-cyclopropylmethyl-1H-benzimidazol-2-ylamine methanesulfonate | 457.1 | described in EXAMPLE 59 (57%). Add to the free base 2 equivalents of methanesulfonic acid essentially as previously described in the General Method for Salt Formation.

MS (ES): m/z=426.2 (M$^+$+1).

The compounds of EXAMPLES 92-99 may be prepared essentially as described in EXAMPLE 77.

| EXAMPLE | Compound | MS (ESI$^+$): m/z = |
|---|---|---|
| 92 | 1-Neopentyl-2-amino-6-(2-(cyclopropyl)-4-phenyl-1H-imidazol-5-yl)-1H-benzimidazole methanesulfonate | 385.0 (M$^+$ + 1) |
| 93 | 1-Neopentyl-2-amino-6-(2-(cyclopropyl)-4-(2,4-difluorophenyl)-1H-imidazol-5-yl)-1H-benzimidazole methanesulfonate | 422.2 (M$^+$ + 1) |
| 94 | 2-Amino-5-[2-(2-chloro-6-fluorophenyl)-4-phenyl-1H-imidazole-5-yl]-3-neopentyl-3H-benzimidazole di-methanesulfonate | 474 (M$^+$ + 1) |
| 95 | 2-Amino-5-[(2-tert-butyl-4-phenyl-1H-imidazole-5-yl]-3-neopentyl-3H-benzimidazole di-methanesulfonate | 402 (M$^+$ + 1) |
| 96 | 2-Amino-5-[2-(2-chloro-6-fluorophenyl)-4-(2,4-difluorophenyl)-1H-imidazole-5-yl]-3-neopentyl-3H-benzimidazole di-methanesulfonate | 510.1 (M$^+$ + 1) |
| 97 | 2-Amino-5-[2-tert-butyl-4-(2,4-difluorophenyl-1H-imidazole-5-yl]-3-neopentyl-3H-benzimidazole di-methanesulfonate | 438.3 (M$^+$ + 1) |
| 98 | 2-Amino-5-[2-(2-fluoro-6-trifluoromethylphenyl)-4-(2,4-difluorophenyl)-1H-imidazole-5-yl]-3-isobutyl-3H-benzimidazole di-methanesulfonate | 530 (M$^+$ + 1) |
| 99 | 6-[2-(2,6-Bistrifluoromethylphenyl)-5-phenyl-1H-imidazol-4-yl]-1-isobutyl-1H-benzimidazol-2-ylamine di-methanesulfonate | 544 (M$^+$ + 1) |

EXAMPLE 100

1-Isobutyl-2-amino-6-(4-(4-fluorophenyl-2H-[1,2,3]triazol-5-yl)-1H-benzimidazole Beginning with 4-(4-fluorophenyl)-5-(3-(isobutylamino)-4-aminophenyl)[1,2,3]triazole, the title compound is prepared essentially as described in EXAMPLE 4.

MS ES): m/z=350.39 (M$^+$+H).

EXAMPLE 101

1-Isobutyl-2-amino-6-(4-(2,4-difluorophenyl-2H-[1,2,3]triazol-5-yl)-1H-benzimidazole methanesulfonate Beginning with 4-(2,4-difluorophenyl)-5-(3-(isobutylamino)-4-aminophenyl)[1,2,3]triazole, the title compound is prepared essentially as described in EXAMPLE 4 and the salt is prepared as described in the general procedure.

MS (ES): m/z=368.38 (M$^+$+H).

EXAMPLE 102

6-(2-Ethoxymethyl-5-phenyl-2H-[1,2,3]triazol-4-yl)-1-isobutyl-11H-benzimidazol-2-ylamine Add cesium carbonate (408 mg, 1.25 mmol) and chloromethyl ethyl ether (0.057 ml, 0.62 mmol) to a solution of 1-isobutyl-2-amino-6-(4-phenyl-2H-[1,2,3]triazol-5-yl)-1H-benzimidazole (208 mg, 0.62 mmol) in DMF (5 mL). Stir for 2 hours at RT, add aqueous ammonium chloride solution (20 ml) and extract with diethyl ether (20 ml). Dry over magnesium sulfate, concentrate and purify (radial silica gel chromatography eluting with hexane:ethyl acetate 1:1) to provide the title compound as a white solid (30 mg, 13%).

MS (ES): m/z=390.48 (M$^+$+H).

EXAMPLE 103

6-(2-Ethoxymethyl-5-phenyl-3H-[1,2,3]triazol-4-yl)-1-isobutyl-1H-benzimidazol-2-yl amine Add cesium carbonate (408 mg, 1.25 mmol) and chloromethyl ethyl ether (0.057 ml, 0.62 mmol) to a solution of 1-isobutyl-2-amino-6-(4-phenyl-2H-[1,2,3]triazol-5-yl)-1H-benzimidazole (208 mg, 0.62 mmol) in DMF (5 tri). Stir for 2 hours at RT, add aqueous ammonium chloride solution (20 ml) and extract with diethyl ether (20 ml). Dry over magnesium sulfate, concentrate and purify (radial silica gel chromatography, eluting with hexane:ethyl acetate 1:1) to provide the title compound as a white solid (32 mg, 13%).

MS (ES): m/z=390.48 (M$^+$+H).

The compounds of EXAMPLES 104-110 may be prepared essentially as described in EXAMPLE 91.

| EXAMPLE | Compound | MS (ESI+): m/z = |
|---|---|---|
| 104 | 2-Amino-5-[3-(4-fluorophenyl)-1-isopropyl-1H-pyrazole]-3-isobutyl-3H-benzimidazole di-methanesulfonate | 392.2 (M + H) |
| 105 | 2-Amino-5-[3-(4-fluorophenyl)-1-tert-butyl-1H-pyrazole]-3-isobutyl-3H-benzimidazole di-methanesulfonate | 406.3 (M + H) |
| 106 | 2-Amino-5-[3-phenyl-1-methyl-1H-pyrazole]-3-isobutyl-3H-benzimidazole di-methanesulfonate | 346.3 (M + H) |
| 107 | 2-Amino-5-(3-phenyl-1-isopropyl-1H-pyrazole)-3-isobutyl-3H-benzimidazole di-methanesulfonate | 374.2 (M + H) |
| 108 | 2-Amino-5-[3-phenyl-1-tert-butyl-1H-pyrazole]-3-isobutyl-3H-benzimidazole di-methanesulfonate | 338.3 (M + H) |
| 109 | 6-[5-(4-Fluorophenyl)-1H-pyrazol-4-yl]-1-isobutyl-2-methyl-1H-benzimidazole di-methanesulfonate | 348.3 (M + H) |
| 110 | 6-[5-(4-Fluorophenyl)-1H-pyrazol-4-yl]-1-isobutyl-1H-benzimidazol-2-ylamine | 349.1 (M + H) |

EXAMPLE 111

1-Isobutyl-2-amino-6-[2-(4-fluorophenyl)-6,7-dihydro-5H-pyrrolo[1,2-a]imidazole-3-yl]benzimidazole di-methanesulfonate To a solution of 3-bromo-2-(4-fluorophenyl)-6,7-dihydro-5H-pyrrolo[1,2-α]imidazole (0.75 g, 2.67 mmol) in DME (20 ml) bubbled with $N_2$, is added $PdCl_2(PPh_3)_2$ (0.175 g, 0.095 mmol). The mixture is stirred at RT for 3 min and 1-isobutyl-2-aminobenzimidazole-6-ylboronic acid (0.75 g, 3.21 mmol) is added followed by a 2N aqueous solution of $Na_2CO_3$ (2.7 mL, 5.40 mmol). Heat the mixture at 90° C. for about 16 h, cooled to RT and diluted with water (50 ml). Extract with EtOAc (150 ml), dry ($Na_2SO_4$), concentrate and purify (HPLC X-Terra MS C18 column, 35 to 50% $CH_3CN$ in $NH_4HCO_3$ 10 mM, pH 9), to give the free amine (0.325 g, 31% yield. MS (ESi+): 390 (M+H)+. Prepared 1-isobutyl-2-amino-6-[2-(4-fluorophenyl)-6,7-dihydro-5H-pyrrolo[1,2-α]imidazole-3-yl]benzimidazole di-methanesulfonate as the title compound following the General Method for Salt Formation (50% yield).

MS (ESi+): 390 (M+H)+.

The compounds of EXAMPLES 112-113 may be prepared essentially as described in EXAMPLE 111.

| EXAMPLE | Compound | MS (ESI+): m/z = |
|---|---|---|
| 112 | 2-Amino-5-[2-phenylimidazo[1,2-a]pyridine-3-yl]-3-(iso-butyl)-3H-benzimidazole di-methanesulfonate | 382.1 (M + H) |
| 113 | 2-Amino-5-[3-(4-fluorophenyl)-1-methyl-1H-pyrazole]-3-isobutyl-3H-benzimidazole | 364.1 (M + H) |

EXAMPLE 114

1-Isobutyl-2-amino-6-(2-(tert-butyl)-4-(4-fluorophenyl)oxazol-5-yl)-1H-benzimidazole methanesulfonate Bubble nitrogen through a suspension of 2-(tert-butyl)-4-(4-fluorophenyl)-5-bromooxazole (2.0 g, 9.1 mmol), 1-isobutyl-2-amino-6-bromobenzimidazole (4.98 g, 18.6 mmol), cesium carbonate (6.06 g, 18.6 mmol), palladium(II) acetate (0.201 g) and triphenylphosphine (1.2 g, 4.5 mmol) in 15 mL dimethylformamide for 3 minutes. Stir the reaction mixture at 100° C. for 18 hours. Cool to room temperature. Partition between ethyl acetate and saturated aqueous sodium chloride. Wash the organic layer with saturated aqueous sodium chloride, dry over sodium sulfate, and concentrate under reduced pressure. Subject the residue to silica gel chromatography, eluting with 50:1 dichloromethane:methanol containing 2M ammonium hydroxide to provide 1-isobutyl-2-amino-6-(2-(tert-butyl)-4-(4-fluorophenyl)oxazol-5-yl)-1H-benzimidazole (1 g, 27%). This material is treated with methanesulfonic acid as previously described to provide the title compound.

MS (ES): m/z=407.2

EXAMPLE 115

1-Isobutyl-2-amino-6-(2-(tert-butyl)-4-(2,4-difluorophenyl)oxazol-5-yl)-1H-benzimidazole methanesulfonate Beginning with 2-(tert-butyl)-4-(2,4-difluorophenyl)-5-bromooxazole and 1-isobutyl-2-aminobenzimidazole-6-boronic acid, the title compound may be prepared essentially as described in EXAMPLE 59.

MS (ES): m/z=425

EXAMPLE 116

1-Isopropylsulfonyl-2-amino-6-(3-phenyl-5-methyl-isoxazol-4-yl)benzimidazole

Beginning with 3-phenyl-4-bromo-5-methylisoxazole and 1-isopropylsulfonyl-2-aminobenzimidazole-6-boronic acid, the title compound may be prepared essentially as described in EXAMPLE 59.

MS (ES): m/z=397.2 (M++H)

Inhibition of p38 Kinase

Standard Solution Preparations

The kinase buffer solution is prepared by combining 2.5 mL 1 M Tris-HCl (pH 7.5), 0.1 mL 1 M dithiothreitol, 1.0 mL 1 M magnesium chloride, and 300 μL 1% Triton X-100 and diluting to 100 mL with water. 84 mL of this kinase buffer solution is combined with 16 mL dimethylsulfoxide to prepare the 16% DMSO solution.

The 200 µM ATP solution is prepared by adding 102.6 mL 10 mM aqueous ATP, 25 µL $^{33}$P-ATP, and 163.5 µL of 4 mM aqueous Epidermal Growth Factor Peptide 661-681 (Biomol, Catalog #P-121) in 5 mL kinase buffer solution.

The p38 kinase enzyme solution is prepared by dissolving 9.5 µL concentrated enzyme solution (250 ng p38 enzyme/µL kinase buffer solution) in 1536 µL kinase buffer solution.

Sample Preparation

An 80 µM solution of each test compound and control compound are prepared by dissolving 2 µL of a 10 mM stock solution of the respective compounds in dimethylsulfoxide in 248 µL of the 16% DMSO solution in a Costar 96-well microtiter plate. The plate is placed onto the Tecan Genesis automated liquid handler for 1:3 serial dilutions.

Assay

10 µL of serially diluted compound is placed with a Beckman Multimek 96-well automated liquid handler to the assay plate. 20 µL of 200 µM ATP solution is added with a Titertek Multidrop 8-channel liquid handler. 10 µL of p38 kinase enzyme solution is transferred to the assay plate using the Multimek. The mixture is allowed to react for 40 minutes at 30° C. and then the reaction is stopped by adding 60 µL of freshly prepared 5% glacial acetic acid with Multidrop. 80 µL of this solution is transferred to an "MAPH" plate using the Multimek. The plates are allowed to set for 30 minutes at room temperature and then washed/aspirated on the Titertek MAP extractor with freshly prepared 0.5% glacial acetic acid (1×300 µl, 2×200 µL). The wells are blotted and 100 µL MicroScint-20 scintillation fluid (Packard Bioscience) is added with the Multidrop. The plates are allowed to sit for 30 minutes and counted on a PE/Wallac Microbeta Trilux scintillation counter for $^{33}$P-isotope.

All exemplified compounds were initially tested at 10 concentrations (20 µM-1 nM using 1:3 serial dilutions). Compounds with $IC_{50}$ values less than 25 nM were re-tested at a starting concentration of 2 µM to 0.1 nM (1:3 serial dilutions). $IC_{50}$ values were calculated (IDBS ActivityBase software) for each compound using non-linear regression. All exemplified compounds were tested essentially as described above and were found to inhibit the p38 kinase enzyme with an $IC_{50}$ of at least 5 µM.

Inhibition of TNF-α in Vitro

Mouse Peritoneal Macrophages 1 mL thioglycolate broth (5.0 g yeast extract, 15.0 g casitone or trypticase, 5.0 g dextrose, 2.5 g sodium chloride, 0.75 g L-cystine, 0.5 g sodium thioglycolate, 1.0 mg resazurin, and 0.75 g agar in 1.0 L distilled water) are injected into the peritoneal cavity of Balb/C female mice. At day 4 or 5 post-injection the mice are sacrificed and then injected i.p. with 4 mL RPMI-1640 medium (BioWhittaker) and the peritoneal macrophages are withdrawn by syringe.

Cytokine Production

Mouse peritoneal microphages are counted with a hemocytometer and adjusted to 5×10$^5$ cells/well in 96-well plates in RPMI-1640 medium with 10% fetal bovine serum. 200 µL/well is plated in 96-well plates and the cells allowed to settle and adhere to the bottom of the well for at least 3 hours. The test compound or standard p38 kinase inhibitor is pre-treated using a series of 8 concentrations for 1 hour at 37° C. (20 µL/well). The cells are treated with a mixture of 50 ng/mL lipopolysaccharide (LPS) and 10 U/mL interferon-γ for 18 hours at 37° C. (20 µL/well). The conditioned media is harvested and assayed for TNF-α production using the Luminex procedure.

TNF-α/Luminex Detection Assay (Bio-Rad Bio-Plex Kit—Catalog #171-G12221)

The lyophilized premixed TNF-α standard (1 standard tube/two 96-well plates) is reconstituted with 50 mL sterile water (500,000 pg/mL). The samples are vortexed for 5 seconds, incubated on ice for 30 minutes, and vortexed for 5 seconds before use. A set of twelve 1.5 ml tubes are labeled with #1-thru #12 and then the amounts of cell media shown below added to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). The premixed anti-cytokine conjugated beads are vortexed (25×) vigorously for 30 seconds. The anti-cytokine conjugated beads are diluted to a 1× concentration using 1× Bio-Plex Assay Buffer. For every plate, 240 µL of the pre-mixed beads is added to 5760 µL of Bio-Plex Assay Buffer. A Millipore 96-well filter plate is blocked with 100 µL/well of blocking buffer. The blocking buffer is filtered through using a Millipore filtration system and then toweled dry. 2 washes are performed on the filter plate with 100 µl/well of Bio-Plex Assay Buffer and toweled dry The 1× anti-cytokine conjugated beads are vortexed for 15 seconds and added 50 µL to each well. This is filtered through and toweled dry. 2 washes are performed on plates with 100 µl/well of Bio-Plex Wash Buffer. Again, it is filtered through and toweled dry. 50 µL of sample or standard is added to each sample well. This is incubated for 60 seconds at room temperature on a shaker protected from light at setting 6 and then for 30 minutes at setting 3 and then placed in the refrigerator overnight. 3 washes are performed with Bio-Plex Wash Buffer. Filter through and toweled dry. The cytokine detection antibody is prepared (~10 minutes prior to use) for every plate and 60 µL of the premixed cytokine detection antibody stock is added to 5940 µL of Bio-Plex Detection Antibody Diluent. 50 µL of cytokine detection antibody is added and incubate for 60 seconds at room temp on a shaker protected from light at setting 6 and then for 30 minutes at setting 3. 3 washes are performed with the Bio-Plex Wash Buffer. This is filtered through and toweled dry. Strept-PE (~10 minutes prior to use) is prepared for every plate and 60 µL to 5940 µL of Bio-Plex Assay Buffer added. 50 µL of Streptavidin-PE is added to each well and incubated for 60 seconds at room temperature on a shaker protected from light at setting 6 and then for 10 minutes at setting 3. 3 washes are performed with Bio-Plex Wash Buffer. This is filtered through. The beads are re-suspended in 100 µL/well of Bio-Plex Assay Buffer. Standards and samples are read on a Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

Representative members of the exemplified compounds were tested essentially as described above and suppressed TNF-α in vitro with an $IC_{50}$ less than 100 nM.

Inhibition of TNF-α in Vivo

Compounds are administered p.o. (100, 30, 10 and 3 mg/kg) to female Balb/c mice (5 mice/dose). After 2 hours, lipopolysaccharide (LPS, *E. coli* serotype 0111:B4, 5 mg/kg) is administered i.v. in the tail vein of each mouse. One hour after LPS administration the mice are asphyxiated by $CO_2$ inhalation and bled out via cardiac puncture.

TNF-α/Luminex Detection Assay (Bio-Rad Bio-Plex Kit—Catalog #171-G12221)

Reconstitute the lyophilized premixed TNF-α standard (1 standard tube/two 96-well plates) with 50 μL sterile water (500,000 pg/mL). Gently vortex for 5 seconds, incubate on ice for 30 minutes, and vortex for 5 seconds before use. Label a set of twelve 1.5 ml tubes with #1-thru #12 and then add the amounts of cell media shown below to the appropriate tubes (standard concentrations are as follows: 50,000; 25,000; 12,500; 6,250; 3,125; 1,562.5; 781.3; 390.6; 195.3; 97.7; 48.8; and 24.4 pg/mL). Vortex the premixed anti-cytokine conjugated beads (25×) vigorously for 30 seconds. Dilute the anti-cytokine conjugated beads to a 1× concentration using 1× Bio-Plex Assay Buffer. For every plate, add 240 μL of the pre-mixed beads to 5760 μL of Bio-Plex Assay Buffer. Block a Millipore 96-well filter plate with 100 μL/well of blocking buffer. Filter through the blocking buffer using a Millipore filtration system. Towel dry. Perform 2 washes on the filter plate with 100 μl/well of Bio-Plex Assay Buffer and towel dry. Vortex the 1× anti-cytokine conjugated beads for 15 seconds and add 50 μL to each well. Filter through and towel dry. Perform 2 washes on plates with 100 μl/well of Bio-Plex Wash Buffer. Filter thru and towel dry. Add 25 μL of serum sample and 25 μL of diluent (Bio-Rad) or 50 μL standard to each sample well. Incubate for 60 seconds at room temperature on a shaker protected from light at setting 6 and then for 30 minutes at setting 3 and then place in the refrigerator overnight Perform 3 washes with Bio-Plex Wash Buffer. Filter through and towel dry. Prepare cytokine detection antibody (~10 minutes prior to use) for every plate, add 60 μL of the premixed cytokine detection antibody stock to 5940 μL of Bio-Plex Detection Antibody Diluent. Add 50 μL of cytokine detection antibody and incubate for 60 seconds at room temp on a shaker protected from light at setting 6 and then for 30 minutes at setting 3. Perform 3 washes with Bio-Plex Wash Buffer. Filter through and towel dry. Prepare strept-PE (~10 minutes prior to use) for every plate, add 60 μL to 5940 μL of Bio-Plex Assay Buffer. Add 50 μL of Streptavidin-PE to each well and incubate for 60 seconds at room temp on a shaker protected from light at setting 6 and then for 10 minutes at setting 3. Perform 3 washes with Bio-Plex Wash Buffer. Filter through. Re-suspend the beads in 100 μL/well of Bio-Plex Assay Buffer. Read standards and samples on Luminex machine. These intensity readings are then converted to picogram/milliliter units based on a 12-point standard curve created in duplicate using a four-parameter logistic regression method (Bio-Plex Manager 2.0, Bio-Rad), and the $IC_{50}$ calculated.

Representative members of the exemplified compounds were tested essentially as described above and suppressed TNF-α in vivo with an $IC_{50}$ less than 100 mg/kg.

Effect on Intra-Articular LPS Induced TNF-α

Intra-articular injection of LPS into rat ankles induces the synthesis of TNF-α, which can be measured in synovial lavage fluid. High levels of TNF-α are detectable within 2 hours. Since the joint is the site where arthritis develops, this model can rapidly determine whether an orally administered compound has an effect on an inflammatory response in the synovium.

Six female Lewis rats (150-200 g) are place in each treatment group. The animals are given vehicle (1% NaCarboxymethylcellulose-0.25% Tween 80) or Example 6 (1 mg/kg, 3 mg/kg, 10 mg/kg, and 30 mg/kg) orally. One hour later, 10 μl LPS (10 μg) is administered intra-articularly into the right ankle of each rat, while the left ankle receives 10 μL of saline. After two hours, each ankle is lavaged with 100 μL of saline. The lavage is collected and stored at −80° C.

Group#1: Vehicle (1% NaCMC-0.25% Tween 80, 1 mL, PO)
Group#2: Example 6 (free base) (1 mg/kg, 1 mL, PO)
Group#3: Example 6 (free base) (3 mg/kg, 1 mL, PO)
Group#4: Example 6 (free base) (10 mg/kg, 1 mL, PO)
Group#5: Example 6 (free base) (30 mg/kg, 1 mL, PO)

TNF-α was measured with a commercially available ELISA kit (R&D, RTA00). Treatment with Example 78 produced a dose-dependent inhibition of TNF-α synthesis, as measured in the synovial lavage fluid. The TMED50=3 mg/kg for the compound of Example 6 in this assay.

B16F10 Melanoma Target (MAPKAP-K2 Phosphorylation) and B16F10 Melanoma Metastasis Efficacy Model Inhibition of B16F10 Melanoma Lung Metastases The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of monodisperse viable cells is determined using a hemocytometer and adjusted to $1 \times 10^6$ cells/ml. Tumor cells are injected intravenously into the tail vein of normal C57B16 mice with an inoculum volume of 0.2 ml containing 200,000 cells. Mice are treated with test compound or vehicle control starting 1 day before i.v. tumor inoculation. The test compound is prepared as a suspension formulation in 1% NaCMC/0.25% polysorbate 80 and probe sonicated in an injection volume of 1% body weight (e.g., the 30 mg/kg dose level is prepared at 3 mg/ml and 0.2 cc was administered per 20 gram mouse). Mice are treated orally tid. with the test compound at 30, 10, and 3 mg/kg (90, 30, and 9 mg/kg/day) from days—1 thru 16 after tumor cell inoculation. Control mice receive the vehicle alone in an identical manner. On day 16, the mice are sacrificed, and the lungs are harvested and fixed in 3% paraformaldehyde. Lung lesions are quantitated by manual counting under a dissecting microscope.

B16F10 Target (Phosphorylated MAPKAPK-2) Studies

The B16F10 melanoma cell line is obtained from the American Type Culture Collection, Rockville, Md. The cells are cultured in RPMI-1640 medium supplemented with 10% fetal calf serum. The cells grown in vitro are harvested during their exponential growth phase by gentle trypsinization, washed twice in medium, and resuspended in serum-free RPMI-1640 medium. The number of viable cells is determined using a hemocytometer and adjusted to $1 \times 10^7$/ml. Tumor cells are injected subcutaneously in normal C57B16 mice. Inoculum volume per mouse is 0.2 mL (2,000,000 cells). When the tumors reach 300-500 mg, the mice are used for target inhibition studies at either a fixed time (2.5 hours) after p.o. compound treatment or pharmacodynamic studies where the tumors are collected at multiple time-points (e.g., 3, 6, 9, 12, 15, and 18 hours) after p.o. compound treatment.

Protein Extraction and Immuno-Blot Analysis

Tumors collected as described above are immediately snap-frozen in liquid nitrogen and stored at 80° C. Tumor tissues are homogenized on ice using a Daunce homogogenizer in an extraction buffer (25 mM Tris pH 7.5 containing the following protease inhibitors: 10 μg/ml leupeptin, 10 μg/ml soybean tryp-chymotrypsin inhibitor, 10 μg/ml N-tosyl-L-phenylalanine chloromethyl ketone, 10 μg/ml aprotinin, Nα-p-tosyl-L-arginine methyl ester, 7 mM benzamidine, 0.3 mM phenylmethylsulfonyl fluoride and two tablets of Roche complete protease inhibitor cocktail; following phosphatase inhibitors: 60 mM beta-glycerophosphate, 1 mM sodium vanadate, 10 mM sodium fluoride. 20 mM p-nitrophenyl phosphate, 1 μM okadaic acid, 1 μM microcystin, 2.5 mM sodium pyrophosphoate; and 1 mM dithiothreitol, 15 mM EDTA, 5 mM EGTA, 1% Triton X100 and 150 mM sodium chloride). Tissue lysates are cleared by centrifugation in a refrigerated microcentrifuge at 14,000 rpm and at 1° C. for 20 minutes. Supernatants are transferred to fresh microfuge tubes prechilled on ice and snap-freeze again in liquid nitrogen or dry ice. After quick thaw to about 80% completion in lukewarm water, the samples are placed on ice to complete thaw. The samples are centrifuged again at 14,000 rpm and at 1° C. for 15 minutes. The supernatant is transferred to fresh prechilled microfuge tubes and protein concentrations are measured using Bio-Rad protein assay reagents using bovine serum albumin as protein standard.

Protein extracts are equalized with the extraction buffer. An equal volume of 2×SDS sample buffer is added to the protein extracts and boiled in a waterbath for 5 minutes. 100 μg of protein extract per sample is used for electrophoresis on 4-20% gradient SDS-PAGE gel and transferred onto nitrocellulose (NC) membranes. NC membranes are blocked in 5% BSA in TBST (20 mM Tris pH7.5, 500 mM sodium chloride, 0.05% Tween 20 and 0.02% sodium azide) for least 1 hour. The membranes are then incubated in primary antibody at 1:1,000 with 5% BSA in TBST overnight on a shaker with 80 rpm at 4° C. Membranes are washed 4×, 10 minutes each, with TBST. The membranes are then incubated for 40 minutes with secondary antibody HRP (horse radish peroxidase) conjugate at 1:10,000 dilution in 3% non-fat milk in TBST and washed again 4 times with TBST, 10 minutes each. The immuno-blots are then visualized by enhanced chemiluminescence (ECL, Amersham) as per manufacturer's instructions. All primary antibodies are purchased from Cell Signaling and secondary antibody HRP conjugates are obtained from Amersham. Gels, membranes and apparatus used for electrophoresis and Western blotting are purchased from Invitrogen. Protein bands of interest are quantified from films using Kodak Image Station 1000.

P815 Tumor Model

Female (6-8 weeks old) DBA/2 mice (Taconic) are implanted subcutaneously into the hind flank region on day 0 with P815 cells ($0.5 \times 10^6$ cells in 200 ul of RPMI 1640). P815 tumor cells are purchased from ATCC and are cultured in RPMI 1640 medium, supplemented with glutamine and 10% bovine serum at 37° C. in 5% CO2 cell culture incubator. Tumor-bearing animals are treated with oral administration of test compound at different doses or vehicle with frequency of three times a day started on the day of implantation. Tumor growth is monitored every 2 days by measuring perpendicular diameters. Tumor volume expressed in milligram (mg) is determined as the product of the largest diameter (a) and its perpendicular (b) according to the formula [tumor volume=$a \times b^2 \times 0.536$].

In Vivo Target Inhibition Study in P815 Mastocytoma Model

In vivo target inhibition is determined by measuring the effect of inhibitor treatment on the phosphorylation of MAP-KAP-K2 expressed in P815 tumor tissues. Tumors in DBA/2 mice received P815 cells subcutaneous implantation are allowed to grow to a size of 300-500 mg without treatment Tumor bearing mice are then given oral administration of test compound or vehicle. To investigate time course related target inhibition by test compound, tumors are harvested from $CO_2$ sacrificed animals at the indicated times (3 hours, 6 hours, 12 hours, and 18 hours) after compound is dosed at 30 mg/kg. Dose-dependent target inhibition by test compound is investigated by harvesting tumors at 3 hours after orally given different doses of test compound or vehicle. Harvested tumors are immediately snap frozen onto dry ice, pulverized, homogenized and lysed in cooled lysis buffer containing proteinase and phosphatase inhibitors. After centrifugation to remove cell debris, supernatants containing 100 microgram total proteins are resuspended in 2× Tris-Glycin loading buffer and subjected to sodium dodecyl sulfate-polyacrylamide gel electrophoresis (10% Tris-Glycine) under reducing conditions. Proteins are subsequently blotted onto a PDVF membrane and were then blocked in 5% milk PBS containing 0.1% Tween-20 for 1 hour at room temperature. The membrane is then incubated with primary antibody (anti-phospho-MAPKAP-K2, Cell Signaling) at 4° C. overnight followed by incubation with secondary antibody (anti-rabbit HRP-conjugated IgG) at room temperature 1 hour. Phospho-MAPKAP-K2 expression level is visualized by Phospho-Image detection system after the enhanced chemiluminescence (ECL) detection is used to reflect the presence of proteins on the PVDF blots. Expression level of phospho-p38 MAP kinase and total p-38 MAP kinase is also monitored by similar western blotting procedure.

Rat Collagen Induced Arthritis Efficacy Model

Female Lewis rats (($\cong$190 gm, Charles River Labs) are immunized with Bovine type II collagen (2 mg/ml) emulsified with an equal volume of adjuvant (aluminum hydroxide). were used. The rats are immunized with approximately 0.3 mg of the emulsion intradermally on the back neat the base of the tail. All animals are re-immunized 7 days later according to the same protocol. The rats begin to develop arthritis (characterized by swell-ling and redness of one or both ankles) from 12 to 14 days after the first immunization. The rats are equally distributed into five treatment groups at the first signs of arthritis and treatment is initiated with each rat dosed bid for 14 days.

Treatment groups:

| Group 1 | Vehicle (1% NaCarboxymethylcellulose + 0.25% Tween 80) 1 mL, PO, Bid × 14 days |
| --- | --- |
| Group 2 | Example 6, 5 mg/kg, 1 mL, PO, Bid × 14 |
| Group 3 | Example 6, 15 mg/kg, 1 mL, PO, Bid × 14 |
| Group 4 | Example 6, 30 mg/kg, 1 mL, PO, Bid × 14 |
| Group 5 | Prednisolone 10 mg/kg, 1 mL, PO, qd × 14 |

Ankle diameter is measured with calipers 5 days a week and recorded. Data is expressed as the area under the curve (AUC) generated from the composite inflammation scores and statistical analysis performed. The compound of EXAMPLE 6 reduced inflammation by 30% at a dose of 30 mg/kg bid.

Oral administration of the compounds of the present invention is preferred. However, oral administration is not the only route or even the only preferred route. For example, transdermal administration may be very desirable for patients who are forgetful or petulant about taking oral medicine, and the intravenous route may be preferred as a matter of convenience or to avoid potential complications related to oral administration. Compounds of Formula I may also be administered by the percutaneous, intramuscular, intranasal or intrarectal route in particular circumstances. The route of administration may be varied in any way, limited by the physical properties of the drugs, the convenience of the patient and the caregiver, and other relevant circumstances (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material that can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations of the present invention may be determined by methods well known to the skilled artisan.

The tablets, pills, capsules, troches, and the like may also contain one or more of the following adjuvants: binders such as povidone, hydroxypropyl cellulose, microcrystalline cellulose, or gelatin; excipients or diluents such as: starch, lactose, microcrystalline cellulose or dicalcium phosphate, disintegrating agents such as: croscarmellose, crospovidone, sodium starch glycolate, corn starch and the like; lubricants such as: magnesium stearate, stearic acid, talc or hydrogenated vegetable oil; glidants such as colloidal silicon dioxide; wetting agents such as: sodium lauryl sulfate and polysorbate 80; and sweetening agents such as: sucrose, aspartame or saccharin may be added or a flavoring agent such as: peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials that modify the physical form of the dosage unit, for example, as coatings. Thus, tablets or pills may be coated with sugar, hydroxypropyl methylcellulose, polymethacrylates, or other coating agents. Syrups may contain, in addition to the present compounds, sucrose as a sweetening agent and certain preservatives, dyes and colorings and flavors. Materials used in preparing these various compositions should be pharmaceutically pure and non-toxic in the amounts used.

The compounds of Formula I are generally effective over a wide dosage range. For example, dosages per day normally fall within the range of about 0.0001 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way. It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound of Formula I:

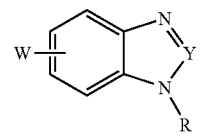

where:

W is a ring selected from the group consisting of:

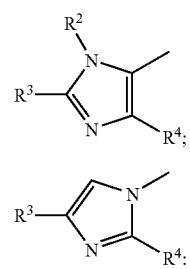

Y is or C—$R^1$;

R is $C_1$-$C_8$ alkyl, $C_3$-$C_6$ cycloalkyl, ($C_1$-$C_4$ alkylene)-($C_3$-$C_6$ cycloalkyl), phenyl, or benzyl optionally substituted on the phenyl ring with one or two substituents selected from halo;

$R^1$ is hydrogen, amino, or methyl;

$R^2$ is hydrogen, $C_1$-$C_6$ alkyl, or $C_3$-$C_6$ cycloalkyl;

$R^3$ is hydrogen, $C_1$-$C_6$ alkyl, $C_3$-$C_6$ cycloalkyl, trifluoromethyl, or phenyl optionally substituted with one or two substituents independently selected from the group consisting of halo, trifluoromethyl, ($C_1$-$C_6$ alkyl)thio, 1-(pyrrolidin-1-yl)eth-2-oxy, and 1-(piperidin-1-yl)eth-2-oxy; or $R^2$ and $R^3$ taken together form either the group —$(CH_2)_n$— where n is 2 or 3 or the group —CH=CH—;

$R^4$ is phenyl optionally substituted with one or two substituents independently selected from the group consisting of halo and trifluoromethyl;

$R^5$ is hydrogen, $C_1$-$C_6$ alkyl, $C_3$-$C_6$ cycloalkyl, or phenyl optionally substituted with one or two substituents independently selected from the group consisting of halo, trifluoromethyl, ($C_1$-$C_6$ alkyl)thio, 1-(pyrrolidin-1-yl) eth-2-oxy, and 1-(piperidin-1-yl)eth-2-oxy;

$R^6$ is hydrogen or ethoxymethyl;

$R^8$ is hydrogen or $C_1$-$C_4$ alkyl; provided that:

when W is imidazole(i), R is C1-C8 alkyl, R2 is hydrogen, R3 is phenyl substituted with one or two substittuents selected from halo;

or a pharmaceutically acceptable salt thereof.

2. A compound of claim 1, where W is a ring of formula (i).

3. A compound of claim 2, where Y is C—$R^1$ and $R^1$ is amino.

4. A compound of claim 3, where R is $C_1$-$C_8$ alkyl.

5. A pharmaceutical formulation comprising a compound of claim 1 in combination with a pharmaceutically acceptable carrier, diluent or excipient.

* * * * *

UNITED STATES PATENT AND TRADEMARK OFFICE
CERTIFICATE OF CORRECTION

Page 1 of 1

PATENT NO. : 7,863,310 B2
APPLICATION NO. : 10/597359
DATED : January 4, 2011
INVENTOR(S) : Rosanne Bonjouklian et al.

It is certified that error appears in the above-identified patent and that said Letters Patent is hereby corrected as shown below:

Cover Page, Column 1 (Inventors), Line 4: Delete "Mirian Filadelfa del Prado Catalina," and insert -- Miriam Filadelfa del Prado Catalina --, therefor.

Column 1, Line 7: Delete "60,563,399" and insert -- 60/563,399 --, therefor.

Column 62, Line 29: In claim 1, after the word "is" delete the word "or".

Column 62, Line 31: In claim 1, delete "cycloalkyl),phenyl," and insert -- cycloalkyl), phenyl, --, therefor.

Column 62, Line 54: In claim 1, delete "C1-C8" and insert -- $C_1$-$C_8$ --, therefor.

Column 62, Line 54: In claim 1, delete "R2" and insert -- $R^2$ --, therefor.

Column 62, Line 55: In claim 1, delete "R3" and insert -- $R^3$ --, therefor.

Column 62, Line 55: In claim 1, delete "substittuents" and insert -- substituents --, therefor.

Signed and Sealed this
Fifteenth Day of March, 2011

David J. Kappos
*Director of the United States Patent and Trademark Office*